United States Patent
Grubb et al.

(10) Patent No.: US 11,690,570 B2
(45) Date of Patent: Jul. 4, 2023

(54) WOUND DRESSING, PATCH MEMBER AND METHOD OF SENSING ONE OR MORE WOUND PARAMETERS

(71) Applicant: Smith & Nephew PLC, Watford (GB)

(72) Inventors: Scott Grubb, Cambridge (GB); Peter Laitenberger, Cambridge (GB)

(73) Assignee: Smith & Nephew PLC, Watford (GB)

( * ) Notice: Subject to any disclaimer, the term of this patent is extended or adjusted under 35 U.S.C. 154(b) by 47 days.

(21) Appl. No.: 16/492,043

(22) PCT Filed: Mar. 9, 2018

(86) PCT No.: PCT/EP2018/055952
§ 371 (c)(1),
(2) Date: Sep. 6, 2019

(87) PCT Pub. No.: WO2018/162736
PCT Pub. Date: Sep. 13, 2018

(65) Prior Publication Data
US 2020/0281529 A1    Sep. 10, 2020

(30) Foreign Application Priority Data

Mar. 9, 2017 (GB) .................................... 1703787
Mar. 9, 2017 (GB) .................................... 1703790

(51) Int. Cl.
*A61B 5/00*    (2006.01)
*A61B 5/1455*    (2006.01)
(Continued)

(52) U.S. Cl.
CPC .......... *A61B 5/6833* (2013.01); *A61B 5/0002* (2013.01); *A61B 5/14552* (2013.01);
(Continued)

(58) Field of Classification Search
CPC . A61B 5/6833; A61B 5/0002; A61B 5/14552; A61B 5/445; A61B 5/7285;
(Continued)

(56) References Cited

U.S. PATENT DOCUMENTS 3,896,802 A    7/1975    Williams
4,334,530 A    6/1982    Hassell
(Continued)

FOREIGN PATENT DOCUMENTS

CN    105232229    1/2016
CN    105395184    3/2016
(Continued)

OTHER PUBLICATIONS

Hu, Fei, Hao, Qi, "Intelligent Sensor Networks: The Integration of Sensor Networks, Signal Processing and Machine Learning", 2013, Auberach Publications, pp. 3-5 (Year: 2013).*
(Continued)

*Primary Examiner* — Eric F Winakur
*Assistant Examiner* — Abid A Mustansir
(74) *Attorney, Agent, or Firm* — Knobbe, Martens, Olson & Bear, LLP

(57) ABSTRACT

In some embodiments, a wound dressing includes at least one motion sensor for sensing a motion related parameter associated with motion of the wound dressing; and at least one further sensor for sensing a healing related parameter associated with wound healing at a region of tissue of a wound or proximate a wound covered by the wound dressing.

20 Claims, 10 Drawing Sheets

(51) Int. Cl.
*A61F 13/02* (2006.01)
*A61M 1/00* (2006.01)

(52) U.S. Cl.
CPC ............ *A61B 5/445* (2013.01); *A61B 5/7285* (2013.01); *A61F 13/0206* (2013.01); *A61M 1/90* (2021.05); *A61B 2560/0214* (2013.01); *A61B 2560/0475* (2013.01); *A61B 2562/0219* (2013.01)

(58) Field of Classification Search
CPC .... A61B 2560/0214; A61B 2560/0475; A61B 2562/0219; A61F 13/0206; A61M 1/0088
See application file for complete search history.

(56) References Cited

U.S. PATENT DOCUMENTS

| | | |
|---|---|---|
| 5,090,410 A | 2/1992 | Saper et al. |
| 5,253,654 A | 10/1993 | Thomas et al. |
| 5,635,201 A | 6/1997 | Fabo |
| 5,642,096 A | 6/1997 | Leyerer et al. |
| 5,678,448 A | 10/1997 | Fullen et al. |
| 5,690,610 A | 11/1997 | Ito et al. |
| 5,836,990 A | 11/1998 | Li |
| 6,095,992 A | 8/2000 | Augustine |
| 6,178,342 B1 | 1/2001 | Borgos et al. |
| 6,381,482 B1 | 4/2002 | Jayaraman et al. |
| 6,517,484 B1 | 2/2003 | Wilk et al. |
| 6,551,252 B2 | 4/2003 | Sackner et al. |
| 6,731,987 B1 | 5/2004 | McAdams et al. |
| 7,014,611 B1 | 3/2006 | Geddes et al. |
| 7,077,832 B2 | 7/2006 | Fleischmann |
| 7,088,591 B2 | 8/2006 | Kishimoto et al. |
| 7,201,063 B2 | 4/2007 | Taylor et al. |
| 7,206,623 B2 | 4/2007 | Blank et al. |
| 7,289,205 B2 | 10/2007 | Yaroslavsky et al. |
| 7,316,652 B2 | 1/2008 | Dalgaard et al. |
| 7,429,255 B2 | 9/2008 | Thompson |
| 7,520,875 B2 | 4/2009 | Bernabei |
| 7,521,292 B2 | 4/2009 | Rogers et al. |
| 7,569,742 B2 | 8/2009 | Haggstrom et al. |
| 7,625,117 B2 | 12/2009 | Haslett et al. |
| 7,687,678 B2 | 3/2010 | Jacobs |
| 7,838,717 B2 | 11/2010 | Haggstrom et al. |
| 7,846,141 B2 | 12/2010 | Weston |
| 7,877,866 B1 | 2/2011 | Greenberg et al. |
| 7,884,258 B2 | 2/2011 | Boehringer et al. |
| 7,904,133 B2 | 3/2011 | Gehman et al. |
| 7,922,676 B2 | 4/2011 | Daskal et al. |
| 7,942,869 B2 | 5/2011 | Houbolt et al. |
| 7,945,302 B2 | 5/2011 | McAdams |
| 8,019,401 B1 | 9/2011 | Smith et al. |
| 8,032,210 B2 | 10/2011 | Finneran et al. |
| 8,060,174 B2 | 11/2011 | Simpson et al. |
| 8,079,247 B2 | 12/2011 | Russell et al. |
| 8,111,165 B2 | 2/2012 | Ortega et al. |
| 8,116,841 B2 | 2/2012 | Bly et al. |
| 8,182,425 B2 | 5/2012 | Stamatas et al. |
| 8,207,392 B2 | 6/2012 | Haggstrom et al. |
| 8,238,996 B2 | 8/2012 | Burnes |
| 8,241,231 B2 | 8/2012 | Bausewein et al. |
| 8,332,053 B1 | 12/2012 | Patterson et al. |
| 8,333,874 B2 | 12/2012 | Currie et al. |
| 8,366,692 B2 | 2/2013 | Weston |
| 8,480,641 B2 | 7/2013 | Jacobs |
| 8,579,872 B2 | 11/2013 | Coulthard et al. |
| 8,644,911 B1 | 2/2014 | Panasyuk et al. |
| 8,663,106 B2 | 3/2014 | Stivoric et al. |
| 8,682,442 B2 | 3/2014 | McAdams |
| 8,783,948 B2 | 7/2014 | Panda et al. |
| 8,788,009 B2 | 7/2014 | Greene et al. |
| 8,800,386 B2 | 8/2014 | Taylor |
| 8,818,478 B2 | 8/2014 | Scheffler et al. |
| 8,829,263 B2 | 9/2014 | Haggstrom et al. |
| 8,848,187 B2 | 9/2014 | Uematsu et al. |
| 8,894,590 B2 | 11/2014 | Lamoise et al. |
| 8,925,392 B2 | 1/2015 | Esposito et al. |
| 8,934,957 B2 | 1/2015 | Dias et al. |
| 8,934,965 B2 | 1/2015 | Rogers et al. |
| 8,943,897 B2 | 2/2015 | Beauvais et al. |
| 8,948,839 B1 | 2/2015 | Longinotti-Buitoni et al. |
| 8,974,428 B2 | 3/2015 | Shuler et al. |
| 8,997,588 B2 | 4/2015 | Taylor |
| 9,000,251 B2 | 4/2015 | Murphy et al. |
| 9,042,075 B2 | 5/2015 | Borini et al. |
| 9,192,531 B2 | 11/2015 | Wu |
| 9,192,700 B2 | 11/2015 | Weston et al. |
| 9,204,806 B2 | 12/2015 | Stivoric et al. |
| 9,220,455 B2 | 12/2015 | Sarrafzadeh et al. |
| 9,226,402 B2 | 12/2015 | Hsu |
| 9,282,897 B2 | 3/2016 | Ross, Jr. et al. |
| 9,314,175 B2 | 4/2016 | Jacofsky et al. |
| 9,320,473 B2 | 4/2016 | Shuler |
| 9,372,123 B2 | 6/2016 | Li et al. |
| 9,378,450 B1 | 6/2016 | Mei et al. |
| 9,386,947 B2 | 7/2016 | Johnson |
| 9,393,354 B2 | 7/2016 | Freedman et al. |
| 9,402,988 B2 | 8/2016 | Buchanan et al. |
| 9,408,573 B2 | 8/2016 | Welch et al. |
| 9,427,179 B2 | 8/2016 | Mestrovic et al. |
| 9,439,599 B2 | 9/2016 | Thompson et al. |
| 9,483,726 B2 | 11/2016 | Mei et al. |
| 9,494,474 B2 | 11/2016 | Servati et al. |
| 9,511,215 B2 | 12/2016 | Skiba |
| 9,516,758 B2 | 12/2016 | Arora et al. |
| 9,526,439 B2 | 12/2016 | Connelly et al. |
| 9,554,484 B2 | 1/2017 | Rogers et al. |
| 9,572,507 B2 | 2/2017 | Moore et al. |
| 9,582,072 B2 | 2/2017 | Connor |
| 9,585,620 B2 | 3/2017 | Paquet et al. |
| 9,587,991 B2 | 3/2017 | Padiy |
| 9,592,007 B2 | 3/2017 | Nuovo et al. |
| 9,603,560 B2 | 3/2017 | Monty et al. |
| 9,610,388 B2 | 4/2017 | Aceto et al. |
| 9,613,911 B2 | 4/2017 | Rogers et al. |
| 9,629,584 B2 | 4/2017 | Barber et al. |
| 9,675,238 B2 | 6/2017 | Iida et al. |
| 9,687,195 B2 | 6/2017 | Sims et al. |
| 9,717,565 B2 | 8/2017 | Blair |
| 9,829,471 B2 | 11/2017 | Hammond et al. |
| 9,907,103 B2 | 2/2018 | Chen et al. |
| 9,999,711 B2 | 6/2018 | Weston et al. |
| 10,004,643 B2 | 6/2018 | Luckemeyer et al. |
| 10,046,096 B2 | 8/2018 | Askem et al. |
| 10,080,524 B1 | 9/2018 | Xi |
| 10,086,117 B2 | 10/2018 | Locke et al. |
| 10,117,705 B2 | 11/2018 | Chernov et al. |
| 10,152,789 B2 | 12/2018 | Carnes et al. |
| 10,182,740 B2 | 1/2019 | Tonar et al. |
| 10,201,644 B2 | 2/2019 | Haggstrom et al. |
| 10,207,031 B2 | 2/2019 | Toth |
| 10,209,213 B2 | 2/2019 | Kang et al. |
| 10,285,620 B2 | 5/2019 | Jung et al. |
| 10,288,590 B2 | 5/2019 | Hammond et al. |
| 10,321,862 B2 | 6/2019 | Dalene et al. |
| 10,463,773 B2 | 11/2019 | Haggstrom et al. |
| 10,857,038 B2 | 12/2020 | Zamierowski et al. |
| 11,026,847 B2 | 6/2021 | Piotrowski et al. |
| 2002/0016536 A1 | 2/2002 | Benni |
| 2002/0135752 A1 | 9/2002 | Sokolov et al. |
| 2003/0033032 A1 | 2/2003 | Lind et al. |
| 2003/0036690 A1 | 2/2003 | Geddes et al. |
| 2003/0036751 A1 | 2/2003 | Anderson et al. |
| 2003/0208148 A1 | 11/2003 | Sullivan |
| 2003/0210810 A1 | 11/2003 | Gee, Jr. et al. |
| 2003/0216630 A1 | 11/2003 | Jersey-Willuhn et al. |
| 2004/0034293 A1* | 2/2004 | Kimball ............... A61B 5/721 600/323 |
| 2004/0230132 A1 | 11/2004 | Shehada |
| 2005/0088832 A1 | 4/2005 | Su et al. |
| 2005/0240107 A1 | 10/2005 | Alfano et al. |
| 2005/0280531 A1 | 12/2005 | Fadem et al. |
| 2005/0281445 A1 | 12/2005 | Marcotte et al. |
| 2006/0052678 A1 | 3/2006 | Drinan et al. |

(56) References Cited

U.S. PATENT DOCUMENTS

| | | |
|---|---|---|
| 2006/0058690 A1 | 3/2006 | Bartnik et al. |
| 2006/0181791 A1 | 8/2006 | Van Beek et al. |
| 2006/0234383 A1 | 10/2006 | Gough |
| 2006/0241495 A1 | 10/2006 | Kurtz |
| 2006/0276700 A1 | 12/2006 | O'Neil et al. |
| 2007/0055209 A1 | 3/2007 | Patel et al. |
| 2007/0173892 A1 | 7/2007 | Fleischer et al. |
| 2007/0191754 A1 | 8/2007 | Aali |
| 2007/0260421 A1 | 11/2007 | Berner, Jr. et al. |
| 2007/0293748 A1 | 12/2007 | Engvall et al. |
| 2008/0081973 A1 | 4/2008 | Hoarau |
| 2008/0167535 A1 | 7/2008 | Stivoric et al. |
| 2008/0258717 A1 | 10/2008 | Igney et al. |
| 2008/0287747 A1 | 11/2008 | Mestrovic et al. |
| 2008/0319282 A1 | 12/2008 | Tran |
| 2008/0319283 A1 | 12/2008 | Cotton et al. |
| 2009/0149800 A1 | 6/2009 | Durand |
| 2009/0177051 A1 | 7/2009 | Arons et al. |
| 2009/0177110 A1 | 7/2009 | Lyden et al. |
| 2009/0209830 A1 | 8/2009 | Nagle et al. |
| 2009/0234206 A1 | 9/2009 | Gaspard et al. |
| 2009/0245601 A1 | 10/2009 | Cohen et al. |
| 2010/0022990 A1 | 1/2010 | Karpowicz et al. |
| 2010/0025831 A1 | 2/2010 | Yamazaki et al. |
| 2010/0166252 A1 | 7/2010 | Ahmed et al. |
| 2010/0168727 A1 | 7/2010 | Hancock et al. |
| 2010/0268111 A1 | 10/2010 | Drinan et al. |
| 2010/0305473 A1 | 12/2010 | Yuzhakov |
| 2011/0004088 A1 | 1/2011 | Grossman |
| 2011/0015591 A1 | 1/2011 | Hanson et al. |
| 2011/0054283 A1 | 3/2011 | Shuler |
| 2011/0092958 A1 | 4/2011 | Jacobs |
| 2011/0130697 A1 | 6/2011 | Nagle et al. |
| 2011/0140703 A1 | 6/2011 | Chiao et al. |
| 2011/0190639 A1 | 8/2011 | Peltie et al. |
| 2011/0218757 A1 | 9/2011 | Callsen et al. |
| 2011/0242532 A1 | 10/2011 | McKenna |
| 2011/0245682 A1 | 10/2011 | Robinson et al. |
| 2011/0301441 A1 | 12/2011 | Bandic et al. |
| 2012/0029306 A1 | 2/2012 | Paquet et al. |
| 2012/0029307 A1 | 2/2012 | Paquet et al. |
| 2012/0029410 A1 | 2/2012 | Koenig et al. |
| 2012/0112347 A1 | 5/2012 | Eckhardt et al. |
| 2012/0165717 A1 | 6/2012 | Al Khaburi et al. |
| 2012/0166680 A1 | 6/2012 | Masoud et al. |
| 2012/0190956 A1 | 7/2012 | Connolly |
| 2012/0190989 A1 | 7/2012 | Kaiser et al. |
| 2012/0265120 A1 | 10/2012 | Beisang, III et al. |
| 2012/0271265 A1 | 10/2012 | Langdon |
| 2012/0277559 A1 | 11/2012 | Kohl-Bareis et al. |
| 2012/0316538 A1 | 12/2012 | Heiser et al. |
| 2012/0330252 A1 | 12/2012 | Stokes et al. |
| 2013/0041235 A1 | 2/2013 | Rogers et al. |
| 2013/0064772 A1 | 3/2013 | Swiss et al. |
| 2013/0121544 A1 | 5/2013 | Sarrafzadeh et al. |
| 2013/0123722 A1 | 5/2013 | Pratt et al. |
| 2013/0151223 A1 | 6/2013 | Zamierowski et al. |
| 2013/0200268 A1 | 8/2013 | Rafferty et al. |
| 2013/0261409 A1 | 10/2013 | Pathak et al. |
| 2013/0271278 A1 | 10/2013 | Duesterhoft et al. |
| 2013/0274629 A1 | 10/2013 | Duesterhoft et al. |
| 2013/0317367 A1 | 11/2013 | Shuler |
| 2014/0012108 A1 | 1/2014 | McPeak |
| 2014/0018637 A1 | 1/2014 | Bennett et al. |
| 2014/0024905 A1 | 1/2014 | Sarrafzadeh et al. |
| 2014/0031663 A1 | 1/2014 | Gallego et al. |
| 2014/0072190 A1 | 3/2014 | Wu et al. |
| 2014/0075658 A1 | 3/2014 | McGuin |
| 2014/0107495 A1 | 4/2014 | Marinelli et al. |
| 2014/0107498 A1 | 4/2014 | Bower et al. |
| 2014/0147611 A1 | 5/2014 | Ackerman, Jr. et al. |
| 2014/0203797 A1 | 7/2014 | Stivoric et al. |
| 2014/0206947 A1 | 7/2014 | Isserow et al. |
| 2014/0232516 A1 | 8/2014 | Stivoric et al. |
| 2014/0235166 A1 | 8/2014 | Molettiere et al. |
| 2014/0243709 A1 | 8/2014 | Gibson et al. |
| 2014/0296749 A1 | 10/2014 | Reid, Jr. et al. |
| 2014/0298927 A1 | 10/2014 | Allin et al. |
| 2014/0298928 A1 | 10/2014 | Duesterhoft et al. |
| 2014/0303463 A1 | 10/2014 | Robinson et al. |
| 2014/0324120 A1 | 10/2014 | Bogie et al. |
| 2014/0340857 A1 | 11/2014 | Hsu et al. |
| 2014/0343478 A1 | 11/2014 | Brennan et al. |
| 2014/0350882 A1 | 11/2014 | Everett et al. |
| 2015/0018792 A1 | 1/2015 | Marsiquet et al. |
| 2015/0025343 A1 | 1/2015 | Gareau et al. |
| 2015/0073271 A1 | 3/2015 | Lee et al. |
| 2015/0138330 A1 | 5/2015 | Krishnamoorthi |
| 2015/0141767 A1 | 5/2015 | Rogers et al. |
| 2015/0148760 A1 | 5/2015 | Dodd et al. |
| 2015/0150479 A1 | 6/2015 | Yoshino et al. |
| 2015/0182166 A1 | 7/2015 | Evans et al. |
| 2015/0223716 A1 | 8/2015 | Korkala et al. |
| 2015/0257644 A1 | 9/2015 | Cao |
| 2015/0265191 A1 | 9/2015 | Harding et al. |
| 2015/0282748 A1 | 10/2015 | Hamaguchi et al. |
| 2015/0292968 A1 | 10/2015 | Vogt et al. |
| 2015/0313476 A1 | 11/2015 | Pisani et al. |
| 2015/0313533 A1 | 11/2015 | Rapp et al. |
| 2015/0327777 A1 | 11/2015 | Kostic et al. |
| 2015/0335254 A1 | 11/2015 | Fastert et al. |
| 2015/0335287 A1 | 11/2015 | Neuman et al. |
| 2015/0335288 A1 | 11/2015 | Toth et al. |
| 2015/0351970 A1 | 12/2015 | Dagger et al. |
| 2015/0359485 A1 | 12/2015 | Berg et al. |
| 2015/0374309 A1 | 12/2015 | Farkas et al. |
| 2016/0015962 A1 | 1/2016 | Shokoueinejad Maragheh |
| 2016/0022223 A1 | 1/2016 | Grundfest et al. |
| 2016/0029900 A1 | 2/2016 | LaPlante et al. |
| 2016/0030132 A1 | 2/2016 | Cheung et al. |
| 2016/0038045 A1 | 2/2016 | Shapiro |
| 2016/0038083 A1 | 2/2016 | Ding et al. |
| 2016/0051147 A1 | 2/2016 | Cohen et al. |
| 2016/0058380 A1 | 3/2016 | Lee et al. |
| 2016/0066854 A1 | 3/2016 | Mei et al. |
| 2016/0069743 A1 | 3/2016 | McQuilkin et al. |
| 2016/0074234 A1 | 3/2016 | Abichandi et al. |
| 2016/0081580 A1 | 3/2016 | Bergelin et al. |
| 2016/0081601 A1 | 3/2016 | Ballam et al. |
| 2016/0100790 A1 | 4/2016 | Cantu et al. |
| 2016/0100987 A1 | 4/2016 | Hartwell et al. |
| 2016/0101282 A1 | 4/2016 | Bergelin et al. |
| 2016/0129469 A1 | 5/2016 | Kulinsky et al. |
| 2016/0143534 A1 | 5/2016 | Hyde et al. |
| 2016/0157779 A1 | 6/2016 | Baxi et al. |
| 2016/0165719 A1 | 6/2016 | Li et al. |
| 2016/0166438 A1 | 6/2016 | Rovaniemi |
| 2016/0213269 A1 | 7/2016 | Lam et al. |
| 2016/0228049 A1 | 8/2016 | Nackaerts et al. |
| 2016/0232807 A1 | 8/2016 | Ghaffari et al. |
| 2016/0242331 A1 | 8/2016 | Park et al. |
| 2016/0249810 A1 | 9/2016 | Darty et al. |
| 2016/0262672 A1 | 9/2016 | Hammond et al. |
| 2016/0262687 A1 | 9/2016 | Vaidyanathan et al. |
| 2016/0270700 A1 | 9/2016 | Baxi et al. |
| 2016/0287177 A1 | 10/2016 | Huppert et al. |
| 2016/0302729 A1 | 10/2016 | Starr et al. |
| 2016/0310023 A1 | 10/2016 | Chachisvilis et al. |
| 2016/0317057 A1 | 11/2016 | Li et al. |
| 2016/0331263 A1 | 11/2016 | Cailler et al. |
| 2016/0331322 A1 | 11/2016 | Son et al. |
| 2016/0338591 A1 | 11/2016 | Lachenbruch et al. |
| 2016/0354001 A1 | 12/2016 | Buckley et al. |
| 2016/0367189 A1 | 12/2016 | Aimone et al. |
| 2016/0367192 A1 | 12/2016 | Iyengar et al. |
| 2016/0367406 A1 | 12/2016 | Barnett |
| 2017/0000407 A1 | 1/2017 | Saxby et al. |
| 2017/0007853 A1 | 1/2017 | Alford et al. |
| 2017/0027498 A1 | 2/2017 | Larson et al. |
| 2017/0079740 A1 | 3/2017 | Hufnagel et al. |
| 2017/0086519 A1 | 3/2017 | Vigano et al. |
| 2017/0086709 A1 | 3/2017 | Khine et al. |
| 2017/0095208 A1 | 4/2017 | Oberleitner et al. |
| 2017/0146474 A1 | 5/2017 | Bedell et al. |

(56) References Cited

U.S. PATENT DOCUMENTS

| | | |
|---|---|---|
| 2017/0156594 A1 | 6/2017 | Stivoric et al. |
| 2017/0156621 A1 | 6/2017 | Bettinger et al. |
| 2017/0156658 A1 | 6/2017 | Maharbiz et al. |
| 2017/0164865 A1 | 6/2017 | Rafferty et al. |
| 2017/0164876 A1 | 6/2017 | Hyde et al. |
| 2017/0172439 A1 | 6/2017 | Zhu et al. |
| 2017/0202711 A1 | 7/2017 | Cernasov et al. |
| 2017/0224271 A1 | 8/2017 | Lachenbruch et al. |
| 2017/0231015 A1 | 8/2017 | Jang et al. |
| 2017/0258972 A1 | 9/2017 | Weston |
| 2017/0304510 A1 | 10/2017 | Askem et al. |
| 2017/0319075 A1 | 11/2017 | Homan et al. |
| 2017/0326004 A1 | 11/2017 | Long et al. |
| 2017/0367644 A1 | 12/2017 | Sharman et al. |
| 2018/0008177 A1 | 1/2018 | Shimuta et al. |
| 2018/0055359 A1 | 3/2018 | Shamim et al. |
| 2018/0055697 A1 | 3/2018 | Mihail et al. |
| 2018/0056087 A1 | 3/2018 | Ribiero et al. |
| 2018/0070880 A1 | 3/2018 | Trembly et al. |
| 2018/0074547 A1 | 3/2018 | Smadi et al. |
| 2018/0116877 A1 | 5/2018 | Ineichen |
| 2018/0128681 A1 | 5/2018 | Otsuka |
| 2018/0132287 A1 | 5/2018 | Cheng et al. |
| 2018/0192514 A1 | 7/2018 | Seo |
| 2018/0200414 A1 | 7/2018 | Askem et al. |
| 2018/0206758 A1 | 7/2018 | Feldkamp et al. |
| 2018/0235484 A1 | 8/2018 | Mozdzierz |
| 2018/0296397 A1 | 10/2018 | Askem et al. |
| 2019/0001032 A1 | 1/2019 | Weston et al. |
| 2019/0021911 A1 | 1/2019 | Askem et al. |
| 2019/0060126 A1 | 2/2019 | Ribble et al. |
| 2019/0076298 A1 | 3/2019 | Quintanar et al. |
| 2019/0083025 A1 | 3/2019 | Aung et al. |
| 2019/0133812 A1 | 5/2019 | Seres et al. |
| 2019/0134280 A1 | 5/2019 | Toth |
| 2019/0159938 A1 | 5/2019 | Askem et al. |
| 2019/0175098 A1 | 6/2019 | Burns |
| 2019/0192066 A1 | 6/2019 | Schoess et al. |
| 2019/0231939 A1 | 8/2019 | Askem et al. |
| 2019/0290496 A1 | 9/2019 | Brownhill et al. |
| 2020/0078499 A1 | 3/2020 | Gadde et al. |
| 2020/0147407 A1 | 5/2020 | Efremkin |
| 2020/0281529 A1 | 9/2020 | Grubb et al. |
| 2020/0330258 A1 | 10/2020 | Hansen et al. |
| 2022/0079814 A1 | 3/2022 | Chen et al. |

FOREIGN PATENT DOCUMENTS

| | | |
|---|---|---|
| CN | 106102322 | 11/2016 |
| DE | 10 2012 211015 | 1/2014 |
| DE | 10 2013 013013 | 2/2015 |
| EP | 2 454 990 | 5/2012 |
| EP | 2 565 630 | 3/2013 |
| EP | 2 574 275 | 4/2013 |
| EP | 1 734 858 | 7/2014 |
| EP | 3 231 478 | 10/2017 |
| EP | 3 409 190 | 12/2018 |
| EP | 3 499 510 | 6/2019 |
| GB | 1476894 | 6/1977 |
| GB | 2316171 | 2/1998 |
| GB | 2563602 | 12/2018 |
| JP | 2006280770 A | 10/2006 |
| JP | 2009-225863 | 10/2009 |
| KR | 10 2012 0119523 | 10/2012 |
| KR | 101224629 B1 | 1/2013 |
| KR | 10 2014 0024743 | 3/2014 |
| KR | 10 2014 0058041 | 5/2014 |
| KR | 10 2016 0071044 | 6/2016 |
| KR | 20190105898 A | 9/2019 |
| NL | 1 027 236 | 4/2006 |
| WO | WO 2000/021433 | 4/2000 |
| WO | WO 2000/043046 | 7/2000 |
| WO | WO-0185024 A1 | 11/2001 |
| WO | WO 2003/067229 | 8/2003 |
| WO | WO 2006/041997 | 4/2006 |
| WO | WO 2007/030379 | 3/2007 |
| WO | WO 2008/006150 | 1/2008 |
| WO | WO 2008/010604 | 1/2008 |
| WO | WO 2009/052607 | 4/2009 |
| WO | WO 2009/120951 | 10/2009 |
| WO | WO 2009/141777 | 11/2009 |
| WO | WO 2010/020919 | 2/2010 |
| WO | WO 2010/105053 | 9/2010 |
| WO | WO 2011/082420 | 7/2011 |
| WO | WO 2011/113070 | 9/2011 |
| WO | WO 2011/123848 | 10/2011 |
| WO | WO 2012/141999 | 10/2012 |
| WO | WO 2013/026999 | 2/2013 |
| WO | WO 2013/044226 | 3/2013 |
| WO | WO 2013/155193 | 10/2013 |
| WO | WO 2014/036577 | 3/2014 |
| WO | WO-2014116816 A1 | 7/2014 |
| WO | WO-2015047015 A1 | 4/2015 |
| WO | WO 2015/112095 | 7/2015 |
| WO | WO 2015/168720 | 11/2015 |
| WO | WO 2016/025438 | 2/2016 |
| WO | WO 2016/030752 | 3/2016 |
| WO | WO 2016/058032 | 4/2016 |
| WO | WO-2016073777 A1 | 5/2016 |
| WO | WO 2016/100218 | 6/2016 |
| WO | WO 2016/109744 | 7/2016 |
| WO | WO 2016/110564 | 7/2016 |
| WO | WO 2016/187136 | 11/2016 |
| WO | WO 2016/205872 | 12/2016 |
| WO | WO 2016/205881 | 12/2016 |
| WO | WO 2017/021006 | 2/2017 |
| WO | WO 2017/021965 | 2/2017 |
| WO | WO 2017/033058 | 3/2017 |
| WO | WO 2017/037479 | 3/2017 |
| WO | WO 2017/041014 | 3/2017 |
| WO | WO 2017/041386 | 3/2017 |
| WO | WO 2017/041387 | 3/2017 |
| WO | WO-2017041385 A1 | 3/2017 |
| WO | WO 2017/119996 | 7/2017 |
| WO | WO 2017/205728 | 11/2017 |
| WO | WO-2017201419 A1 | 11/2017 |
| WO | WO 2017/214188 | 12/2017 |
| WO | WO 2018/035612 | 3/2018 |
| WO | WO 2018/060417 | 4/2018 |
| WO | WO 2018/064569 | 4/2018 |
| WO | WO 2018/115461 | 6/2018 |
| WO | WO 2018/144938 | 8/2018 |
| WO | WO 2018/144941 | 8/2018 |
| WO | WO 2018/144943 | 8/2018 |
| WO | WO 2018/144946 | 8/2018 |
| WO | WO 2018/162728 | 9/2018 |
| WO | WO 2018/162732 | 9/2018 |
| WO | WO 2018/162735 | 9/2018 |
| WO | WO 2018/162736 | 9/2018 |
| WO | WO 2018/185138 | 10/2018 |
| WO | WO 2018/189265 | 10/2018 |
| WO | WO 2018/209090 | 11/2018 |
| WO | WO 2018/210692 | 11/2018 |
| WO | WO 2018/210693 | 11/2018 |
| WO | WO 2018/211458 | 11/2018 |
| WO | WO 2018/234443 | 12/2018 |
| WO | WO 2019/020550 | 1/2019 |
| WO | WO 2019/020551 | 1/2019 |
| WO | WO 2019/020666 | 1/2019 |
| WO | WO 2019/030384 | 2/2019 |
| WO | WO 2019/048624 | 3/2019 |
| WO | WO 2019/048626 | 3/2019 |
| WO | WO 2019/048638 | 3/2019 |
| WO | WO 2019/063481 | 4/2019 |
| WO | WO 2019/063488 | 4/2019 |
| WO | WO 2019/067264 | 4/2019 |
| WO | WO 2019/072531 | 4/2019 |
| WO | WO 2019/076967 | 4/2019 |
| WO | WO 2019/096828 | 5/2019 |
| WO | WO 2019/140441 | 7/2019 |
| WO | WO 2019/140444 | 7/2019 |

(56) References Cited

FOREIGN PATENT DOCUMENTS

| WO | WO 2019/140448 | 7/2019 |
|----|----------------|--------|
| WO | WO 2019/140449 | 7/2019 |

OTHER PUBLICATIONS

International Search Report and Written Opinion, re PCT Application No. PCT/EP2018/055952, dated Aug. 21, 2018.

International Preliminary Report on Patentability for Application No. PCT/EP18/055952, dated Sep. 19, 2019, 11 pages.

"Little Miss Plasters", kidstravelclub.co.uk., accessed Aug. 26, 2016, in 2 pages. URL: http://www.kidstravelclub.co.uk/little-miss-girls-childrens-plasters.

Aubakir, B. et al., "Vital Sign Monitoring Utilizing Eulerian Video Magnification and Thermography", 2016 38th Annual International Conference of the IEEE Engineering in Medicine and Biology Society, Aug. 16, 2016, pp. 3527-3530, in 4 pages.

Bandodkar, A. et al., "Battery-free, skin-interfaced microfluidic/electronic systems for simultaneous electrochemical, colorimetric, and volumetric analysis of sweat", Science Advances, vol. 5(1), Jan. 18, 2019, in 16 pages. URL: http://advances.sciencemag.org/content/5/1/eaav3294.

Cauwe, M. et al., "Technology development for a low-cost, roll-to-roll chip embedding solution based on PET foils", 18th European Microelectronics and Packaging Conference (EMPC), IEEE, Sep. 12, 2011, in 6 pages.

Farooqui, M. et al., "Low Cost Inkjet Printed Smart Bandage for Wireless Monitoring of Chronic Wounds", Scientific Reports, vol. 6, Jun. 29, 2016, in 14 pages.

Geng, Y. et al., "A Hybrid Low Power Biopatch for Body Surface Potential Measurement", IEEE Journal of Biomedical and Health Informatics, vol. 17(3), May 1, 2013, XP011506375.

Great Britain Office Action and Search Report, re GB Application No. 1703787.0, dated Aug. 14, 2017.

Great Britain Office Action and Search Report, re GB Application No. 1703790.4, dated Jul. 18, 2017.

Iannetta, R.A. et al., "Successful case histories of polymer based circuitry on flexible film substrates", Electro/94 International Conference Proceedings Combined Volumes, IEEE, May 10-12, 1994, XP010149465.

Jinto, G. et al., "Reliability of Plastic-Encapsulated Electronic Components in Supersaturated Steam Environments", IEEE Transactions on Components, Packaging, and Manufacturing Technology, vol. 5, No. 10, Oct. 2015, in 9 pages.

Lu, B. et al., "A study of the autofluorescence of parylene materials for [mu]TAS applications", Lab on Chip, vol. 10, No. 14, Jul. 2010, pp. 1826-1834, in 9 pages.

McLeod, A. et al., "Motion Magnification for Endoscopic Surgery", Progress in Biomedical Optics and Imaging, SPIE—International Society for Optical Engineering, Mar. 12, 2014, vol. 9036, in 8 pages.

Mostafalu, P. et al., "Wireless Flexible Smart Bandage for Continuous Monitoring of Wound Oxygenation", IEEE Transactions on Biomedical Circuits and Systems, vol. 9, No. 5, Oct. 2015, pp. 670-677, in 8 pages.

Narusawa, H., "The corona discharge causes short destruction that had bad influence on a power switching circuit", Adphox Corporation, Jan. 1, 2009, in 12 pages. URL: http://www.adphox.co.jp/keisokuki/ke-english-corona/CORONA_DISCHARGE_EN.pdf.

Raviglione, A. et al., "Real-Time Smart Textile-Based System to Monitor Pressure Offloading of Diabetic Foot Ulcers", Journal of Diabetes Science and Technology, vol. 11, Sep. 2017, in 5 pages.

Rose, D. et al., "Adhesive RFID Sensor Patch for Monitoring of Sweat Electrolytes", IEEE Transactions on Biomedical Engineering, vol. 62(6), Jun. 2015 (first published Nov. 11, 2015), in 9 pages.

Wakita, J. et al., "Variations in Optical Absorption and Fluorescence Spectra for Polyimide Thin Films Caused by Structural Isomerism", J. Photopolym. Sci. Technol. Jan. 1, 2003, in 1 page.

Willis, B., "Conformal Coating Inspection & Coating Faults", Vision Engineering, Jul. 21, 2016, in 35 pages. URL: http://www.visioneng.com/wp-content/uploads/2017/11/Confirmal-Coating-Inspection-and-Defects.21JUL16.pdf.

Willis, B., "Guide to Conformal Coating & Cleaning Defects Contents", Mar. 1, 2014, in 31 pages. URL: http://coatingguide.smartgroup.org/Files%20pdf/Coating%20Defects%20V2%2014March2014.pdf.

Mehmood N., et al., "Applications Of Modern Sensors And Wireless Technology In Effective Wound Management: Modern Sensors And Wireless Technology," Journal of Biomedical Materials Research Part B, vol. 102, May 1, 2014, XP055739544, pp. 885-895.

* cited by examiner

WOUND DRESSING, PATCH MEMBER AND METHOD OF SENSING ONE OR MORE WOUND PARAMETERS

CROSS-REFERENCE TO RELATED APPLICATIONS

This application is a U.S. national stage application of International Patent Application No. PCT/EP2018/055952, filed Mar. 9, 2018, which claims the benefit of GB Application No. 1703787.0, filed Mar. 9, 2017, and GB Application No. 1703790.4, filed Mar. 9, 2017.

This disclosure relates to a wound dressing, a patch member configured to be secured to a patient's body proximate to a wound, and a method of sensing at least one parameter associated with a wound or a region of tissue proximate a wound.

Wound healing is natural process performed by the human body in response to injury. The amount of time taken for a wound to heal is dependent on many different factors which include the human body's ability to heal itself and the treatments that may be applied in order to accelerate wound healing. Understanding the healing status of a wound and being able to monitor the healing process helps to inform decisions on further treatment of the wound and can also assist in the development of future wound therapies.

One factor that is known to be associated with wound healing is the amount of blood that is supplied to blood vessels, such as capillaries, within tissue at or near a wound. The process of supplying blood to blood vessels within tissue is known as blood perfusion. Oxygen and nutrients carried by blood within wounded tissue are essential for wound healing and so the amount of blood perfusion is known to correlate well with wound healing. The amount of blood perfusion is typically a measure of a parameter associated with a volume of blood that is supplied to tissue during each cardiac cycle or over a predetermined period of time. Various techniques have been developed for determining an amount of blood perfusion in tissue. For example, it is known that oxygen saturation is correlated with blood perfusion and so spectroscopy techniques such as near-infrared imaging have been developed to monitor oxygen saturation in a wound and the surrounding tissue. However, such conventional techniques require specialist equipment that is typically bulky, expensive and must be operated by an experienced operator. Therefore, when used to inspect a wound, a patient must regularly attend a clinic at which the equipment is located for assessment of wound healing. They are also susceptible to movement of a patient, which can lead to erroneous results. The techniques are therefore unsuitable for frequent periodic assessments of a patient or long-term assessments of a patient when at home.

Various techniques have been developed to monitor healing status and healing progress of a wound. Such techniques rely on specialist optical equipment that is typically bulky, expensive and must be operated by an experienced clinician. Such techniques are therefore unsuitable for frequent periodic assessments of a patient or long-term assessments of a patient when at home.

It is an aim of the present disclosure to at least partly mitigate the above-mentioned problems.

It is an aim of certain embodiments of the present disclosure to provide a means to assess wound healing at or proximate a wound that does not interfere with a patient's daily activities.

It is an aim of certain embodiments of the present disclosure to provide a reliable and accurate means to assess wound healing at or proximate a wound which is not adversely affected by motion of a patient.

It is an aim of certain embodiments of the present disclosure to provide a small, portable, easy to use, inexpensive and disposable means for monitoring wound healing.

It is an aim of certain embodiments of the disclosure to provide a means for remote automated monitoring of wound healing.

According to some embodiments, there is provided a wound dressing comprising at least one motion sensor for sensing a motion related parameter associated with motion of the wound dressing; and at least one further sensor for sensing a healing related parameter associated with wound healing at a region of tissue of a wound or proximate a wound covered by the wound dressing.

The healing related parameter may be a parameter associated with blood perfusion within the region of tissue.

The healing related parameter may be a parameter associated with oxygen saturation of blood within the region of tissue.

The wound dressing may further comprise a processing element for processing an output of the motion sensor and/or an output of the further sensor.

The processing element may be configured to determine that the output of the motion sensor satisfies a predetermined condition corresponding to a predetermined amount of motion of the wound dressing.

The predetermined condition may correspond to a rate of acceleration of the wound dressing which is less than a predetermined rate of acceleration.

The wound dressing may comprise a memory element and the processing element is configured to generate data which corresponds to an output of the motion sensor and data which corresponds to an output of the further sensor and to store said data in the memory element.

The data which corresponds to an output of the motion sensor and data which corresponds to an output of the further sensor may be generated from contemporaneous outputs from the motion sensor and the further sensor.

The processing element may be configured to retain stored data corresponding to an output of the further sensor only when the output of the motion sensor satisfies the predetermined condition corresponding to a predetermined amount of motion of the wound dressing.

The processing element may be configured to discard data corresponding to an output of the further sensor when the output of the motion sensor fails to satisfy the predetermined condition corresponding to a predetermined motion of the wound dressing.

The stored data may be associated with a trace associated with the output of the motion sensor and a trace associated with the output of the further sensor over a sample period.

The sample period may be not less than one second. The sample period may be not less than two seconds. The sample period may be not less than five seconds. The sample period may be not less than ten seconds.

The sample period may be not greater than sixty seconds. The sample period may be not greater than thirty seconds. The sample period may be not greater than fifteen seconds.

The memory element may be configured to store data representing the predetermined condition.

The wound dressing may further comprise a transmitter configured to transmit data stored in the memory element to a remote receiver.

The further sensor may be an optical sensor. The further sensor may be a pulse oximeter sensor. The motion sensor may comprise an accelerometer. The accelerometer may be a multiple axes accelerometer.

The wound dressing may be an island-type dressing having a central wound protecting portion which, in use, overlies a wound and a border portion.

According to some embodiments, there is provided a patch member configured to be secured to a portion of a patient's body proximate a wound, the patch comprising: at least one motion sensor for sensing a motion related parameter associated with motion of the patch member; and at least one further sensor for sensing a characteristic associated with wound healing at a region of tissue of the portion of the patient's body to which the patch member is secured.

According to some embodiments, there is provided a wound monitoring method comprising the steps: sensing a motion related parameter associated with motion of a patient and a healing related parameter associated with wound healing at a region of tissue of the patient at or proximate to a wound; determining that the sensed motion related parameter satisfies a predetermined condition corresponding to a predetermined amount of motion of the patient; and storing and/or transmitting data which represents the sensed healing related parameter associated with wound healing.

The step of sensing the motion related parameter and healing related parameter may comprise the step of monitoring the motion related parameter and the healing related parameter over a sample period.

The sample period may be not less than one second. The sample period may be not less than two seconds. The sample period may be not less than five seconds. The sample period may be not less than ten seconds.

The sample period may be not greater than sixty seconds. The sample period may be not greater than thirty seconds. The sample period may be not greater than fifteen seconds.

The predetermined condition corresponding to a predetermined amount of motion of the patient may be a condition in which the acceleration of the patient or the portion of the patient comprising the region of tissue at or proximate to the wound is below a threshold value.

The motion related parameter may be a pulse frequency of pulsatile arterial blood flow through the target region of tissue and the predetermined condition corresponding to a predetermined amount of motion of the patient is a predetermined pulse frequency.

The healing related parameter may be associated with an amount of oxygen saturation at the region of tissue at or proximate to the wound.

The stored data may be data collected over a sample period in which the sensed motion related parameter satisfies the predetermined condition.

The method may further comprise a learning step in which the sample period is set based on attributes of the patient.

The predetermined condition may correspond to a predetermined amount of motion of the patient is set based on attributes of the patient.

The method may further comprise subsequently repeating the steps of sensing the motion and healing related parameters, determining that the motion related parameter satisfies the predetermined condition and storing data representing the parameter associated with wound healing to compile a plurality of records of data associated with wound healing.

The method may further comprise the step of transmitting the data comprising the plurality of records to a remote device for processing.

According to some embodiments, there is provided a wound dressing comprising at least one motion sensor for sensing a motion related parameter associated with motion of the wound dressing; at least one further sensor for sensing a healing related parameter associated with wound healing at a region of tissue of a wound or proximate a wound covered by the wound dressing; and a processing element for processing an output of the motion sensor and/or an output of the further sensor, the processing element configured to: determine if the output of the motion sensor satisfies a predetermined condition corresponding to a predetermined amount of motion of the wound dressing; in response to determining that the output of the motion sensor satisfies the predetermined condition, retain data corresponding to the output of the further sensor; and in response to determining that that output of the motion sensor fails to satisfy the predetermined condition, discard the data corresponding to the output of the further sensor.

According to some embodiments, there is provided a wound monitoring method comprising the steps: sensing a motion related parameter associated with motion of a patient and a healing related parameter associated with wound healing at a region of tissue of the patient at or proximate to a wound; determining if the sensed motion related parameter satisfies a predetermined condition corresponding to a predetermined amount of motion of the patient; in response to determining that the sensed motion related parameter satisfies the predetermined condition, storing and/or transmitting data which represents the sensed healing related parameter associated with wound healing; and in response to determining that the sensed motion related parameter fails to satisfy the predetermined condition, discarding the data which represents the sensed healing related parameter associated with wound healing.

According to some embodiments, there is provided a wound dressing comprising: at least one first sensor for sensing a first parameter associated with a wound or a region of tissue proximate a wound; at least one processing element; at least one memory element, and at least one energy storage device for storing energy and supplying energy to at least one of the first sensor, the processing element and the memory element, wherein the processing element is configured to process an output of the first sensor and to store data associated with the output in the memory element.

The energy storage device may comprise a battery. The energy storage device may comprise a capacitor. The energy storage device may comprise a fuel cell.

The wound dressing may further comprise an energy generator. The energy generator may be configured to generate energy from movement of the wound dressing. The energy generator may comprise an electromagnetic energy generator arranged to generate energy from movement of the wound dressing and to store energy in the energy storage device.

The wound dressing may further comprise an accelerometer configured to sense motion of a body to which the wound dressing is secured.

The energy generator may comprise a piezo electric generator.

The energy generator may be a thermoelectric generator configured to generate electrical energy from a temperature difference between the temperature of a body to which the wound dressing is applied and ambient temperature.

The wound dressing may further comprise a transmitter for transmitting data stored in the memory element.

The first sensor may comprise a pulse sensor. The pulse sensor may comprise a pulse oximeter sensor.

The first sensor may be one of a plurality of sensors comprising the wound dressing for sensing a first parameter associated with a wound or a region of tissue proximate a wound.

According to some embodiments, there is provided a method of sensing at least one parameter associated with a wound or a region of tissue proximate a wound, comprising the steps of: securing a wound dressing comprising a wound protecting portion over a wound whereby the wound protecting portion overlies the wound such that the wound dressing is fixed with respect to the wound; sensing a parameter associated with the wound or a region of tissue proximate the wound using a sensor integral to the wound dressing; processing an output of the sensor using a processing element integral to the wound dressing; and storing data from the processing element in a memory element integral to the wound dressing.

The steps of sensing, processing and storing may be repeated to compile a plurality of records of data associated with the wound.

The method may further comprise a step of sensing motion of a body to which the wound dressing is secured using an accelerometer integral to the wound dressing.

The method may further comprise the step of generating energy using an energy generator configured to generate energy from movement of the wound dressing from movement of the wound dressing.

The energy generated by the energy generator may be stored in an energy storage device integral to the wound dressing.

According to some embodiments, there is provided a method of sensing at least one parameter associated with a wound or a region of tissue proximate a wound, comprising the steps of: sensing a parameter associated with the wound or a region of tissue proximate the wound using a sensor integral to a wound dressing, the wound dressing comprising a wound protecting portion secured over a wound whereby the wound protecting portion overlies the wound such that the wound dressing is fixed with respect to the wound; processing an output of the sensor using a processing element integral to the wound dressing; and storing data from the processing element in a memory element integral to the wound dressing.

The steps of sensing, processing and storing may be repeated to compile a plurality of records of data associated with the wound.

The method may further comprise a step of sensing motion of a body to which the wound dressing is secured using an accelerometer integral to the wound dressing.

The method may further comprise the step of generating energy using an energy generator configured to generate energy from movement of the wound dressing from movement of the wound dressing.

The energy generated by the energy generator may be stored in an energy storage device integral to the wound dressing.

According to some embodiments, there is provided a method of sensing at least one parameter associated with a wound or a region of tissue proximate a wound, comprising the steps of: sensing a parameter associated with the wound or a region of tissue proximate the wound using a sensor integral to a wound dressing, the wound dressing comprising a wound protecting portion secured over a wound whereby the wound protecting portion overlies the wound such that the wound dressing is fixed with respect to the wound; processing an output of the sensor using a processing element integral to the wound dressing; and storing data from the processing element in a memory element integral to the wound dressing, wherein the sensor comprises a pulse sensor.

According to some embodiments, there is provided a wound dressing comprising: at least one first sensor for sensing a first parameter associated with a wound or a region of tissue proximate a wound; at least one processing element; at least one memory element, and at least one energy storage device for storing energy and supplying energy to at least one of the first sensor, the processing element and the memory element, wherein the processing element is configured to process an output of the first sensor and to store data associated with the output in the memory element, wherein: the wound dressing further comprises an energy generator, the energy generator comprises an electromagnetic energy generator arranged to generate energy from movement of the wound dressing and to store energy in the at least one energy storage device, and the first sensor comprises a pulse sensor.

According to some embodiments, there is provided a wound dressing comprising: at least one first sensor for sensing a first parameter associated with a wound or a region of tissue proximate a wound; at least one processing element; at least one memory element, and at least one energy storage device for storing energy and supplying energy to at least one of the first sensor, the processing element and the memory element, wherein the processing element is configured to process an output of the first sensor and to store data associated with the output in the memory element; and an accelerometer configured to sense motion of a body to which the wound dressing is secured, wherein the first sensor comprises a pulse sensor.

Certain embodiments of the present disclosure allow for a parameter associated with wound healing to be sensed when it is determined that any motion of a body or portion of a body of a patient to which a wound dressing in accordance with certain embodiments of the disclosure is applied will not adversely affect the measurement obtained.

Certain embodiments of the present disclosure allow for wound healing to be assessed when a body or part of a body of a patient to which a wound dressing in accordance with certain embodiments of the disclosure is applied is determined to be motionless.

Certain embodiments of the present disclosure allow for wound healing to be monitored without interfering with a patient's daily activities.

Certain embodiments of the present disclosure allow for data associated with a wound or a region of tissue proximate a wound, such as data associated with wound healing, to be collected and stored by a wound dressing for processing or subsequent retrieval.

Certain embodiments of the present disclosure allow for data associated with wound or a region of tissue proximate a wound, such as data associated with wound healing, to be collected and stored by a wound dressing over a prolonged period of time or intermittent periods of time without having to be connected to an external power source or external device during the periods of time or between the intermittent periods of time.

Embodiments of the present disclosure will now be described, by way of example only, with reference to the accompanying drawings in which.

Figure 1:
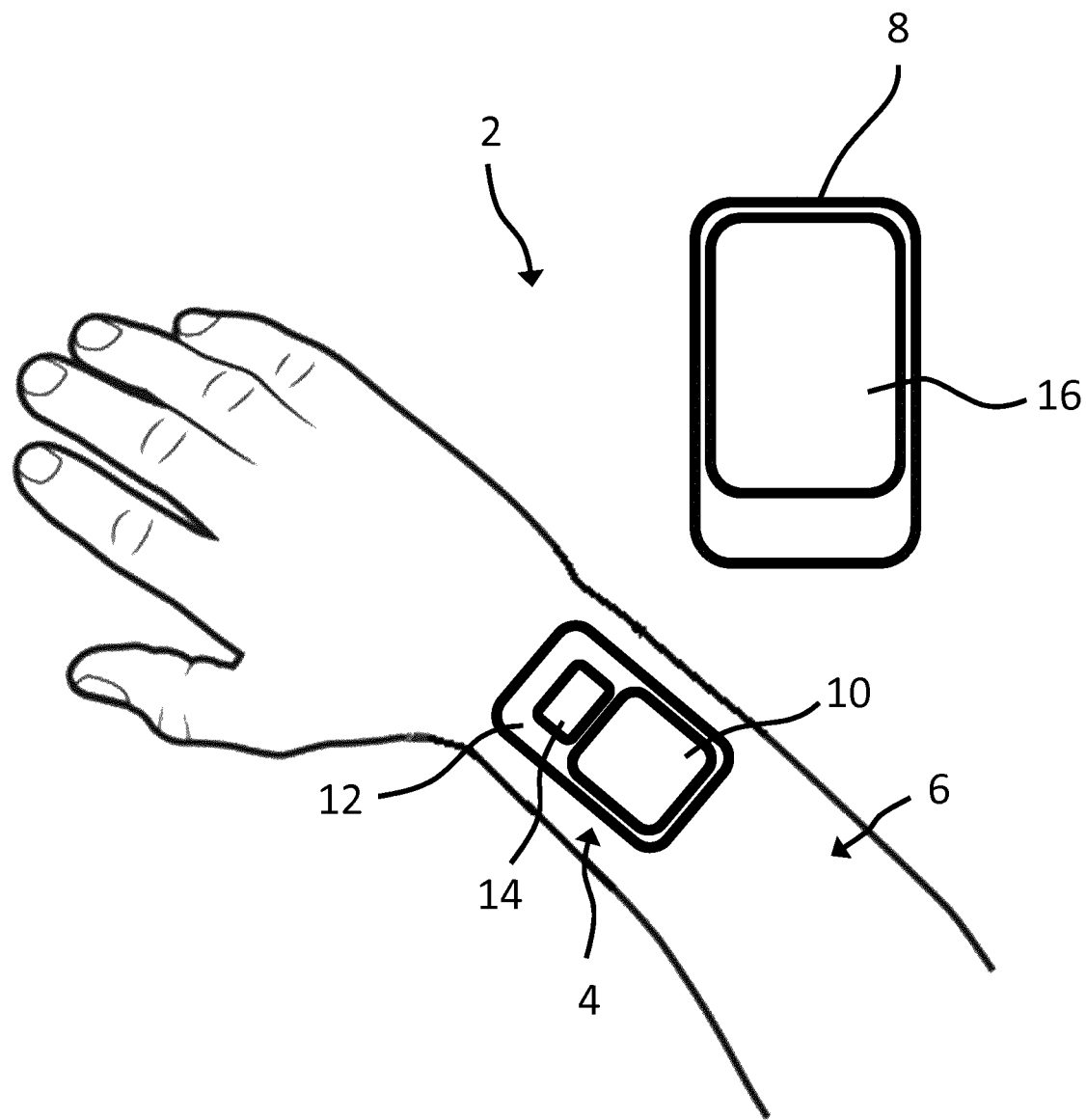
FIG. 1 is a schematic representation of apparatus comprising a wound dressing and a monitoring device in use.

FIG. 1 shows apparatus 2 comprising a wound dressing 4 secured to a patient's arm 6, and a monitoring device 8.

The wound dressing 4 includes a wound contact layer which extends across a whole lower surface of the wound dressing and a cover layer that likewise extends across the whole of the wound dressing 4. The wound dressing 4 comprises a central wound protecting portion 10 spaced away from an edge of the wound dressing 4, a peripheral securing portion 12 and a sensor module 14 which is formed integrally with the securing portion 12. The central wound protecting portion 10 may comprise one or multiple internal layers according to use such as, but not limited to wound exudate absorbing layers, fluid transport layers, spacer layers and/or anti-bacterial layers. The securing portion 12 has an adhesive on its lower surface for securing the wound dressing 4 to the arm 6 of the patient.

The monitoring device 8 has an integrated display 16 on which information is displayed to a user. The monitoring device 8 may be a hand-held device and may be a smartphone or tablet running a monitoring app.

Figure 2:
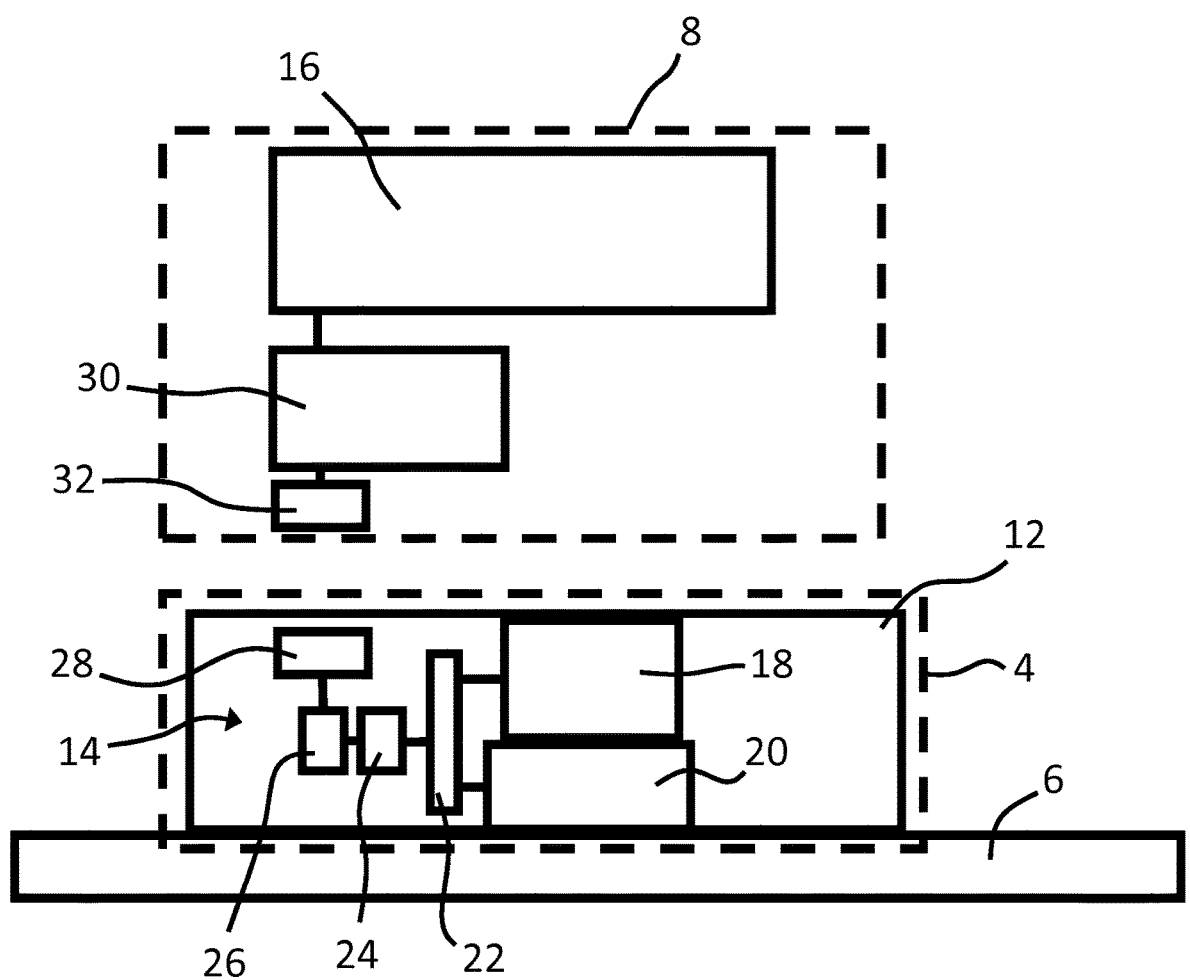
FIG. 2 is a schematic representation of key components of the apparatus shown in FIG. 1.

FIG. 2 is a system diagram representing certain components of the apparatus 2 shown in FIG. 1. Components of the wound dressing 4 and the monitoring device 8 are enclosed, respectively, by broken lines.

The sensor module 14 comprises a first sensor in the form of a motion sensor 18 for sensing motion of the sensor 18 and a second sensor which is an optical sensor 20 for sensing a parameter corresponding to wound healing. In the example described this is a parameter associated with oxygen saturation ($SpO_2$), at a target region of the skin tissue of the arm 6 underneath the optical sensor 20. The position of the motion sensor 18 is fixed with respect to the optical sensor 20, wound protecting portion 10, and peripheral securing portion 12 such that they move together. In the embodiment shown, the motion sensor 18 is a single-axis accelerometer and the optical sensor 20 is a pulse oximeter sensor. The sensor module 14 further comprises signal processing electronics 22 connected to the sensors 18, 20, a first controller or processor 24 configured to process an output from the signal processing electronics 22, a data storage device in the form of a memory element 26, and a transmitter 28. Outputs from the motion sensor 18 and the optical sensor 20 is received by the signal processing electronics 22 before being processed by the first processor 24.

In addition to the display 16, the monitoring device 8 comprises a second controller or processor 30 and a receiver 32 for receiving signals transmitted by the transmitter 28. The signals may be transmitted wirelessly via a short-range communication protocol.

Figure 3:
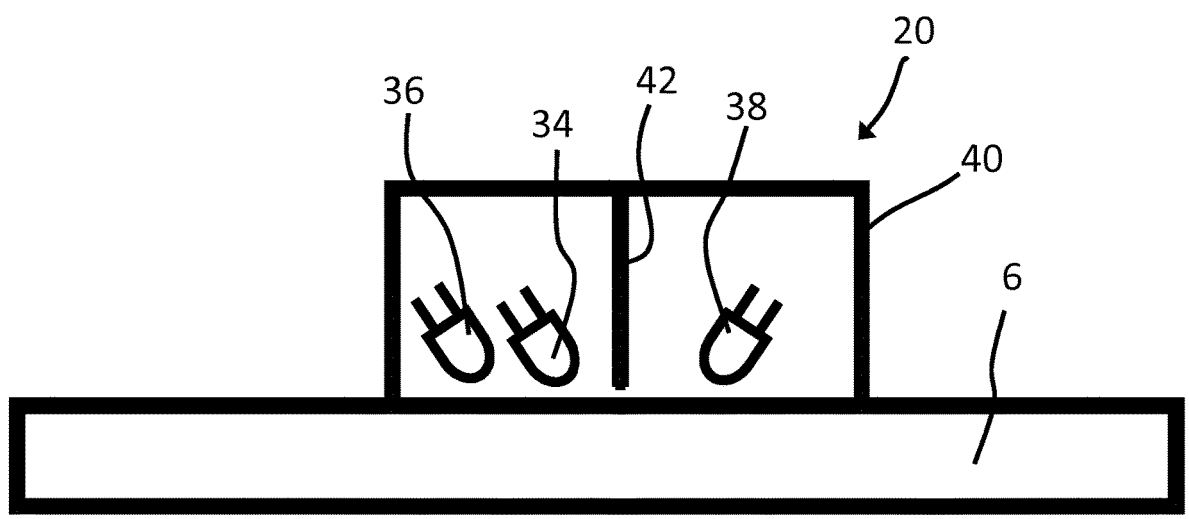
FIG. 3 is a schematic representation of a sensor for sensing a parameter associated with wound healing.

FIG. 3 is a schematic representation of the optical sensor 20. The optical sensor 20 comprises two light emitters in the form of a first light emitting diode (first LED) 34 and a second light emitting diode (second LED) 36, and a light detector in the form of a photodiode 38.

The first LED 34 is configured to emit light in the near-infrared and/or infrared band of the visible spectrum, for example, light having a centre wavelength of 905 nm. The second LED 36 is configured to emit light in the red band of the visible spectrum, for example, light having a centre wavelength of 660 nm. Other numbers of LEDs and other suitable wavelengths could be utilised.

The photodiode 38 is configured to detect light at the wavelengths of light emitted by the first and second LEDs 34, 36.

The first and second LEDs 34, 36 and the photodiode 38 are disposed within a housing 40 and are separated by a shield 42 which is opaque to the wavelength or range of wavelengths of light detectable by the photodiode 38. The shield 42 prevents emitted light from being transmitted directly to the photodiode 38. The lower portion of the housing 40 is open or transparent so that light emitted by the first and second LEDs 34, 36 can pass through the lower portion to the skin tissue of the arm 6 and light reflected or scattered by the skin tissue of the arm 6 can pass back through the lower portion of the housing 40 to the photodiode 38. The shield 42 is spaced slightly from the skin tissue so that it does not contact the skin and so does not prevent light from passing underneath the shield 42. Light received by the photodiode 38 is therefore light which has been emitted by at least one of the LEDs 34, 36 and either reflected, scattered or absorbed and reemitted by the skin tissue of the arm 6.

A method of determining a parameter associated with an amount of skin perfusion in tissue surrounding a wound area using the apparatus 1 will now be described with reference to FIGS. 1 to 6.

In use, the wound dressing 4 is secured to the patient's arm 6 over a wound, as shown in FIG. 1, so that the lower portion of the housing 40 of the optical sensor 20, which is open or transparent, is adjacent the target area of skin tissue, as shown in FIGS. 2 and 3.

The first and second LEDs 34, 36 emit light towards the skin tissue of the arm 6 at each of their respective wavelengths. The light is then either reflected, scattered or absorbed by the skin tissue depending on the wavelength of the light and the absorption/scattering characteristics of the skin tissue and the blood within the skin tissue.

For instance, the skin tissue can be expected to contain both arterial and venous blood. The amount of venous blood within the tissue remains substantially constant throughout the duration of a cardiac cycle (or varies independently of the cardiac cycle). The arterial blood, however, varies in accordance with the cardiac cycle such that a pressure pulse of arterial blood is created each time the heart pumps blood to the tissue.

It is this pulsatile arterial blood which delivers oxygen to the wound area and so it is the amount of oxygen saturation of pulsatile arterial blood which provides an indicator of wound healing.

At least some of the light which is not absorbed by the skin tissue or the blood within the skin tissue is reflected towards the photodiode 38.

The photodiode 38 produces an output signal which represents the amount of reflected light received by the photodiode 38 from each LED 34, 36.

The signal therefore has two components: an infrared/near-infrared component (referred to hereafter as infrared component for clarity) which represents the amount of reflected light received from the first LED 34 and a red component which represents the amount of reflected light received from the second LED 36. The signal may be a time-multiplexed signal or a combined signal that comprises both components.

Figure 5:
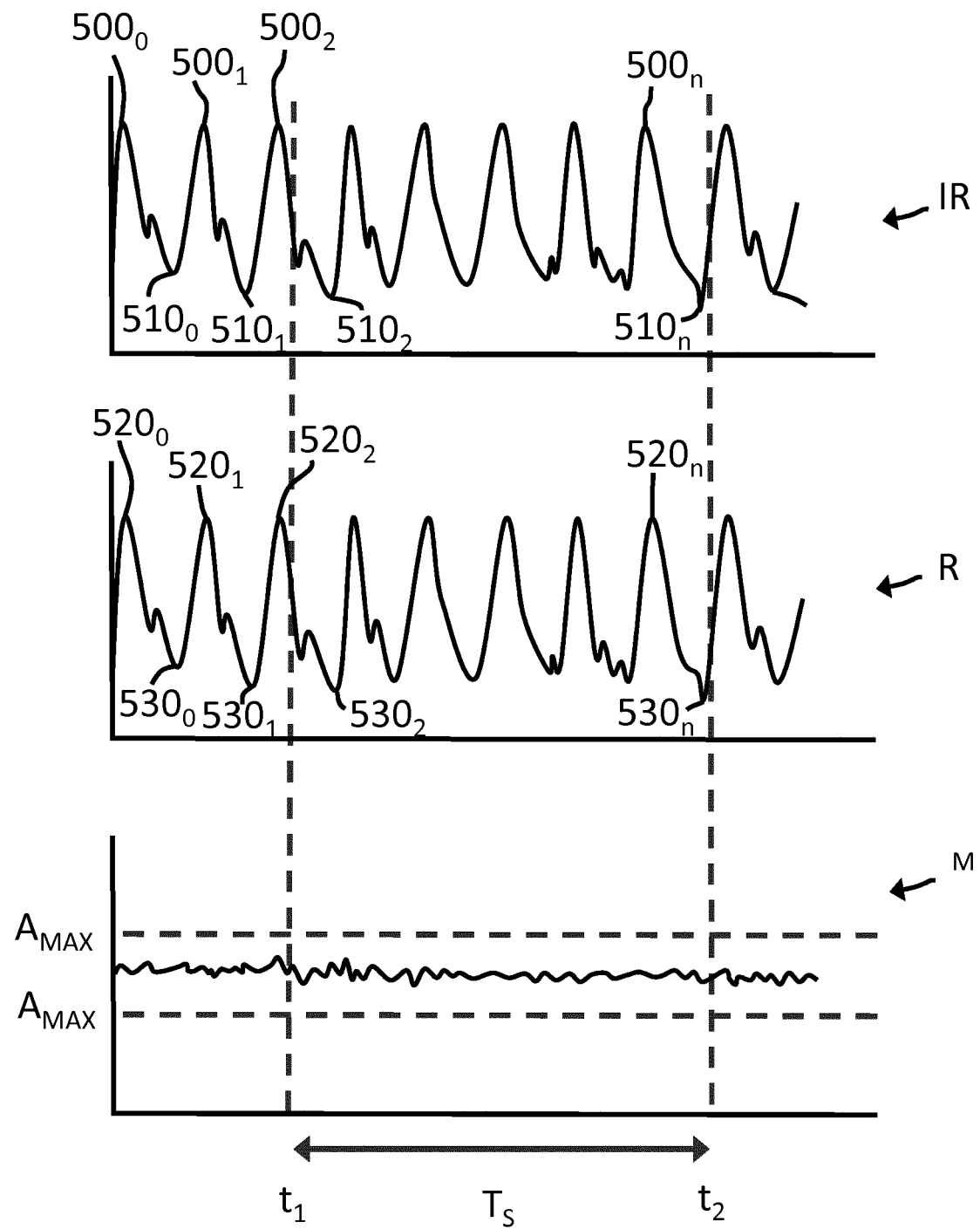
FIG. 5 is an example of an output produced by the apparatus shown in FIG. 1.

FIG. 5 shows traces IR, R which represent the components of the output from the optical sensor 20. Trace IR represents a component of the output from the optical sensor 20 which is indicative of the amount of infrared light emitted by the first LED 34 that is received by the photodiode 38. Trace R represents a component of the output from the optical sensor 20 which is indicative of the amount of red light emitted by the second LED 36 which is received by the photodiode 38. Each trace IR, R comprises a series of regular pulses which represent pulsation of arterial blood through the underlying tissue.

Each of the traces IR, R has a pulsatile component (which represents the amount of light absorbed by the pulsatile arterial blood) and a non-pulsatile component (which represents the amount of light skin tissue, and non-pulsatile arterial and venous blood). The peaks $500_{0,1,2\ldots n}$ of the trace IR are spaced apart with a frequency dependent upon the physiology of the patient. The peaks $520_{0,1,2\ldots n}$ of the R trace are also spaced apart with a same frequency as the peaks of the IR trace which is dependent on the physiology of the patient. The troughs $510_{0,1,2\ldots n}$ of the IR trace and the troughs $530_{0,1,2\ldots n}$ of the R trace are associated with the respective non-pulsatile components (in the absence of a pulsatile component) and therefore provide an indication of the amount of light absorbed at each frequency by the skin tissue and non-pulsatile blood.

Trace M shows a component of the output signal of the motion sensor 18 which represents acceleration of the motion sensor 18. In this instance, the trace M represents acceleration along a single axis. The components of the outputs from the motion sensor 18 and the optical sensor 20 represented by each trace IR, R, M may are isolated from the respective output signals by the signal processing electronics 22 before being processed by the first processor 24. In this sense the trace M amplitude, time variation and/or the peak to peak value can be used to determine how still a patient is.

Figure 4:
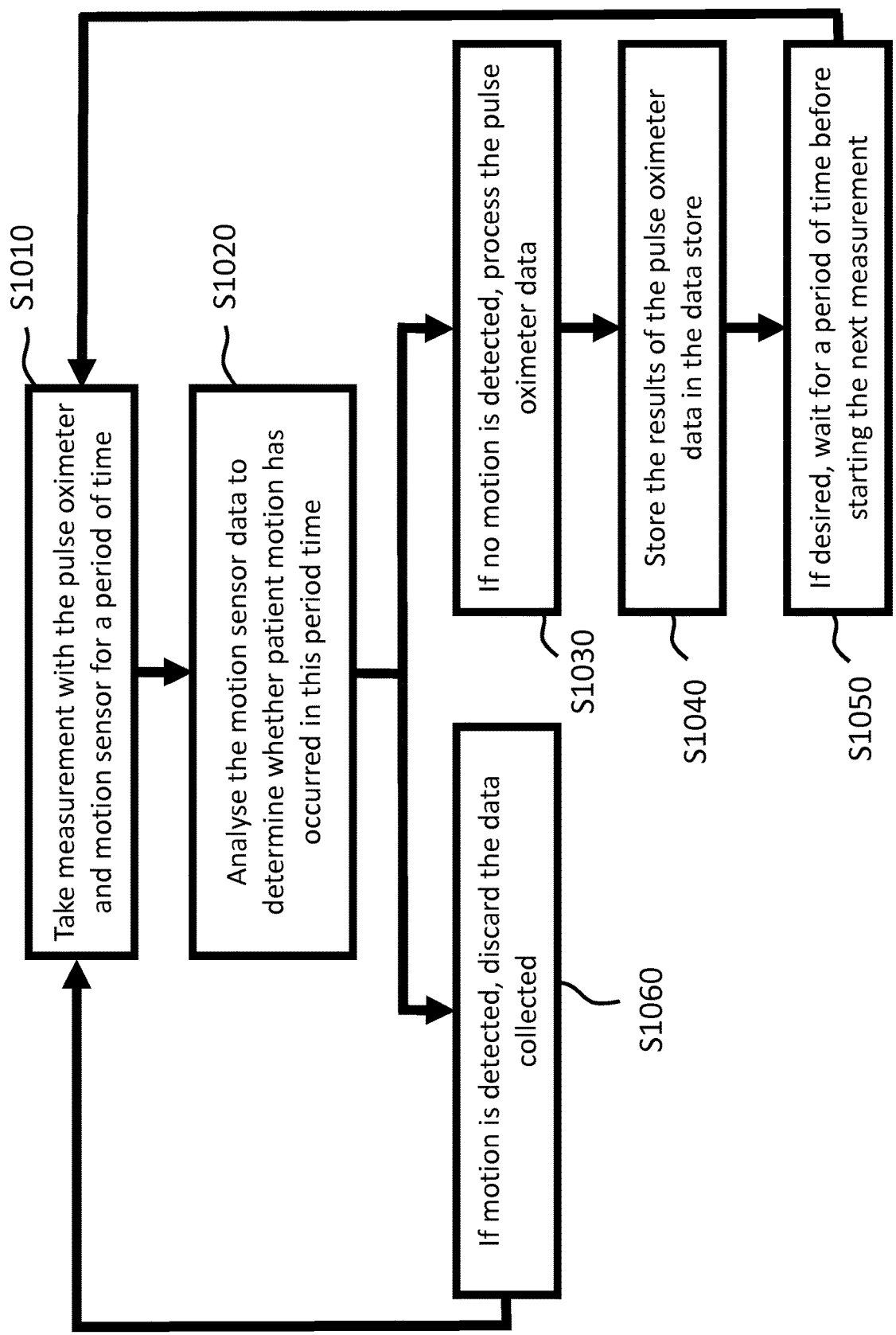
FIG. 4 is a flow chart depicting a method of monitoring wound healing at a target region.

FIG. 4 is a flow chart illustrating a process of obtaining a measurement and subsequently processing the measurement. In order to take a measurement in accordance with step S1010, the first processor 24 starts recording the outputs of the sensors 18, 20 simultaneously at time $t_1$. Referring to FIG. 5, at time $t_2$, after a predetermined period of time $T_S$ has elapsed, the first processor 24 stores the monitored outputs of the sensors 18, 20 obtained over the predetermined period of time $T_S$ temporarily in the memory element 26. The predetermined period of time $T_S$ defines a sampling period over which data is collected and should be set to include at least one pulse of pulsatile arterial blood within the sample data, and may be set to include a plurality of pulses of arterial blood, for example at least 2, 5 or 10 pulses. An adult typically has a heart rate of between 40 and 100 beats per minute. The predetermined period of time $T_S$ may therefore be at least one second, such as at least two, five or ten seconds. It will be appreciated that the longer the predetermined period of time $T_S$, the greater the chance of movement of the patient and hence wound dressing 4. Consequently, the predetermined period of time $T_S$ should be not greater than sixty seconds, for example not greater than thirty seconds or not greater than fifteen seconds. In the embodiment shown, the predetermined period of time $T_S$ is ten seconds which is sufficiently to obtain a good quality data sample without a high risk of the patient moving to an extent that the quality and accuracy of the data is adversely affected. In order to improve accuracy multiple data samples could be combined. The data sampling rate for each trace IR, R, M is between several Hz and several tens of kHz.

As illustrated by step S1020, the trace M obtained over the predetermined period of time $T_S$ is analysed by the first processor 24 to determine whether the motion sensor 18, and hence the wound dressing 4, has experienced motion during the sampling period which could be expected to result in an erroneous or misrepresentative reading by the optical sensor 20. Any disturbance, noise or change in the output of the optical sensor leading to an erroneous or inaccurate reading due to the motion that is detected is known as a "motion artefact". A motion artefact may be caused by a patient standing up, walking or carrying out a task which involves moving a part of the body to which the wound dressing 4 is secured. Different criteria can be used to determine that the motion sensor 18 has moved and hence that a motion artefact is present in the sample. In the embodiment shown, it is determined that a motion artefact is present if the amplitude of the motion trace M exceeds a predetermined threshold amplitude $A_{MAX}$ during the sampling period.

In the example shown in FIG. 5, the motion trace M does not contain a motion artefact. The small fluctuations shown in the trace M is associated with signal noise which may be caused sensor noise or electronics noise or by very small movements that would not be expected to adversely affect measurements. The amplitude of the trace M remains below the threshold amplitude $A_{MAX}$ between $t_1$ and $t_2$. The trace M indicates that no significant movement of the arm 6 has occurred during the sampling period. The components of the output of the optical sensor 20 are therefore processed by the processor 24 to determine the oxygen saturation value ($SpO_2$) of the pulsatile arterial blood, as illustrated by step S1030 shown in FIG. 4.

In order to determine the amount of pulsatile blood in the target area, the pulsatile component for each of the infrared IR and red R traces is normalised with respect to the non-pulsatile component. Typically, this can be done by determining a ratio of the pulsatile component to the non-pulsatile component of the signal. Once the first and second components have been normalised, the ratio of the normalised red R component to the normalised infrared IR component is calculated. The ratio can then be used to determine an oxygen saturation value ($SpO_2$) for the pulsatile arterial blood within the tissue at the target area. For example, the ratio can be converted into an oxygen saturation value ($SpO_2$) value in accordance with the Beer-Lambert law, as is known in the art of spectroscopy. The oxygen saturation value is then stored in the memory 26, as illustrated by step S1040. The measurement step S1010 may then be repeated immediately or after a set period of time has elapsed, as illustrated by step S1050.

Figure 6:
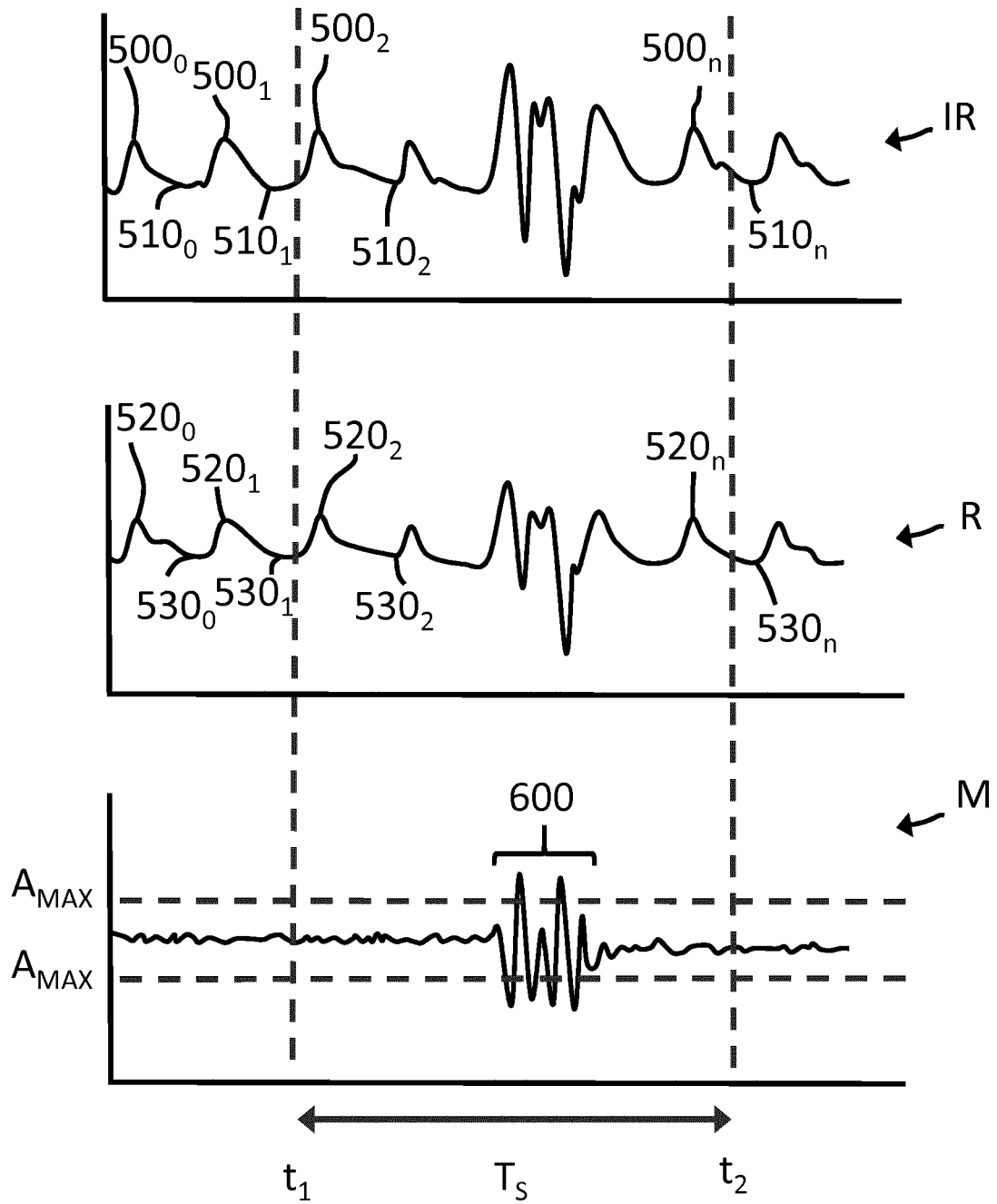
FIG. 6 is a further example of an output produced by the apparatus shown in FIG. 1.

FIG. 6 shows traces IR, R, M comprising a sample period in which a motion artefact is present. A portion 600 of the motion trace M within the predetermined time period $T_S$ comprises multiple oscillations in which the amplitude of the trace M exceeds the predetermined threshold amplitude $A_{MAX}$. The first processor 24 therefore determines that a motion artefact is present. In this case, the motion artefact corresponds with the patient moving his/her arm relatively rapidly for example when lifting an object. However, a motion artefact may also be identified when a patient moves his/her entire body such as walking up a stairway even when the arm does not move significantly with respect to the head, torso, etc. of the patient. In either case, the quality of the data obtained is likely to be adversely affected due to movement of the wound dressing and hence optical sensor 20 with respect to the skin tissue of the patient or because of an increase in blood flow caused by activity of the patient. The measurement is therefore discarded and the first processor 24 deletes the stored outputs from the memory element 26, as illustrated by step S1060. The process of taking a measurement (steps S1010 and S1020) may then be repeated, either immediately or after a further predetermined time, until a motion trace M is obtained in which no motion artefact is present.

Measurements may be taken periodically, for example on a minute-by-minute, hourly, daily or weekly basis and a record of the oxygen saturation ($SpO_2$) values stored on the memory element 26. The stored data can then be transmitted by the transmitter 28 to the receiver 32 of the monitoring device 8 for subsequent processing by the second processor 30 and display on the display 16. For example, the repeated measurements may be used to determine trends that can be subsequently used to determine how well a wound is healing. In the embodiment shown, the monitoring device 8 is a portable handheld device such as a smartphone, tablet or bespoke device having an integrated display in the form of a screen. Alternatively, the stored data may be transmitted via a mobile or wireless network for subsequent processing. Transmission may utilise wireless protocols such as Bluetooth™ Wi-Fi™, Zigbee™, near-field communication or the like may be used. The data or data trends can be visualised, compared to previous readings or incorporated into the records of the patient and an assessment of the wound healing can be carried out.

The wound dressing 4 is compact and lightweight and so will not hinder the patient greatly. Furthermore, the wound dressing 4 need not be removed from the patient in order to inspect the wound and assess healing progress. The wound dressing 4 may be applied to other regions of a patient's body having a wound including another limb such as a leg or a torso or a head or a foot or a hand or other region.

Figure 7:
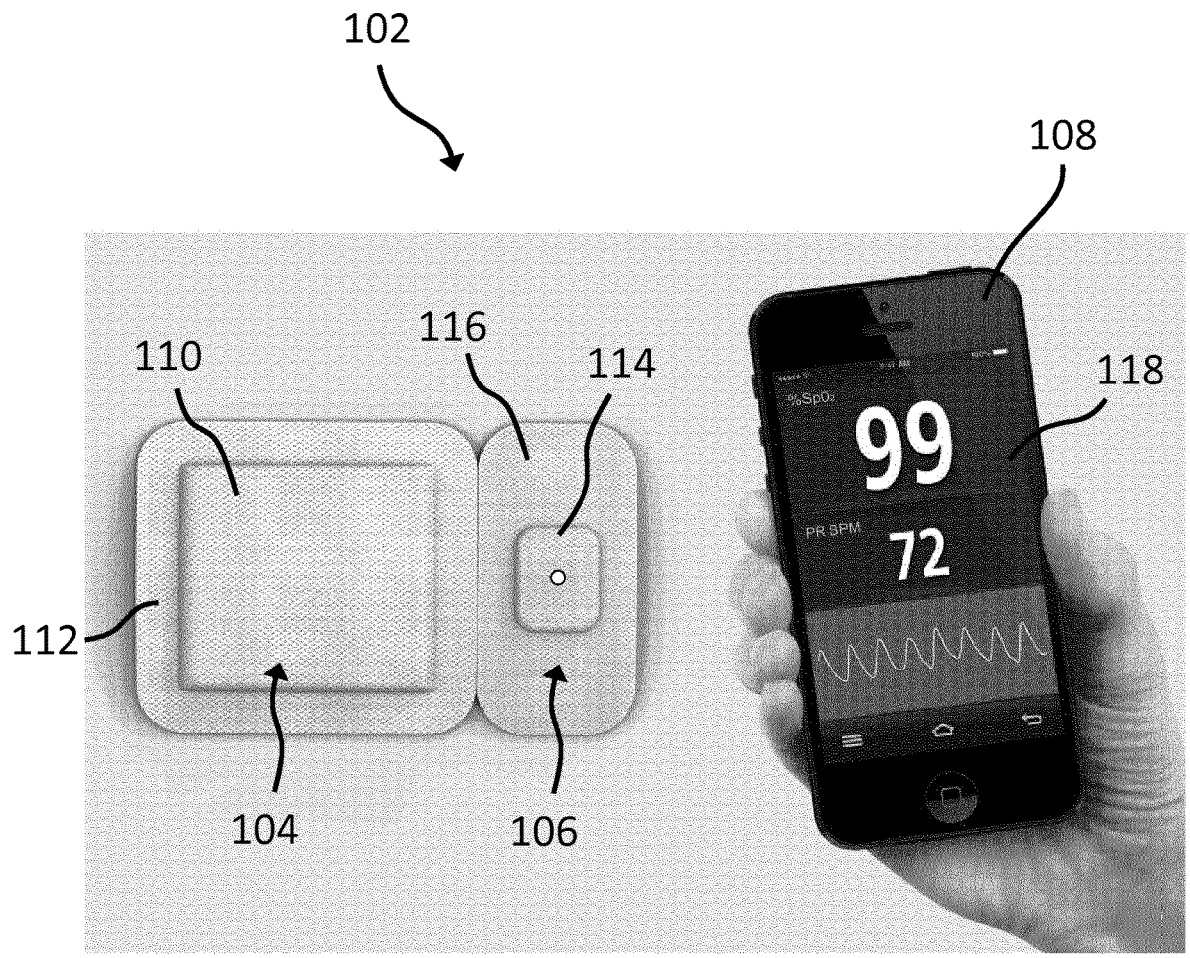
FIG. 7 shows a further embodiment of an apparatus comprising a wound dressing and a monitoring device.

FIG. 7 shows a further embodiment of an apparatus 102 comprising a wound dressing 104, a sensor patch 106 and a monitoring device 108. The wound dressing 104 comprises a central wound protecting portion 110 and a peripheral securing portion 112 or border. The sensor patch 106 comprises a sensor module 114 and a further securing portion 116. The securing portion 112 and the sensor patch 106 have an adhesive on respective lower surfaces for securing them to the body of a patient. The sensor module 114 is in accordance with the sensor module 14 shown in FIGS. 1 and 2. The monitoring device 108 is a handheld device having an integrated display 118. The sensor patch 106 can be secured to a patient's skin adjacent the wound dressing 104. An advantage of the arrangement is that the wound dressing 104 can be changed periodically without having to remove the sensor patch 106. In the embodiment show, the sensor module 114 is wireless and is configured to communicate with the monitoring device 108. The sensor patch 106 can be connected to the wound dressing 104 in a non-removable way or via a releasable connection such as a perforated line. Alternatively, the wound dressing 104 and the sensor patch 106 may be separate. For example, the sensor patch may comprise part of a band or cuff that can be wrapped around a portion of a patient's body, such as a limb.

Figure 8:
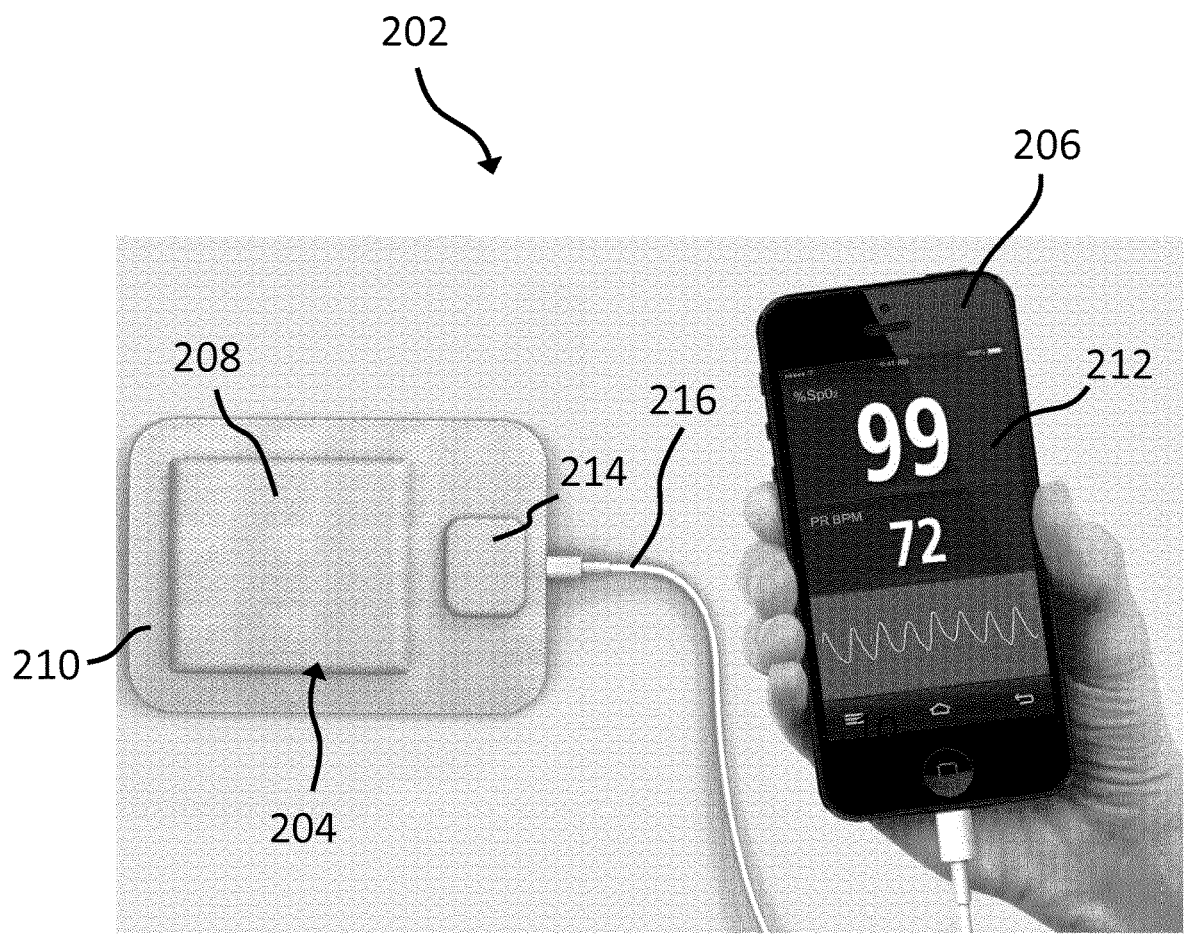
FIG. 8 shows a further embodiment of an apparatus comprising a wound dressing and a monitoring device.

FIG. 8 shows a further embodiment of an apparatus 202 comprising a wound dressing 204 and a monitoring device 206. The wound dressing 204 comprises a wound protecting portion 208, a peripheral securing portion 210 and a sensor module 214 which is formed integrally with the securing portion 210. The securing portion 210 has an adhesive on its lower surface for securing the wound dressing 204 to the arm of a patient. The monitoring device 206 comprises an integrated display 212. A lead 216 is connected to the sensor module 214 at one end and to the monitoring device 206 at the other end. The lead 216 provides a means for communication between the sensor module 214 and the monitoring device 206 and may also provide a means of supplying power to the sensor module 214. In such an embodiment, data may be transmitted directly to the monitoring device and so a processor need not be provided in the wound dressing itself.

Figure 9:
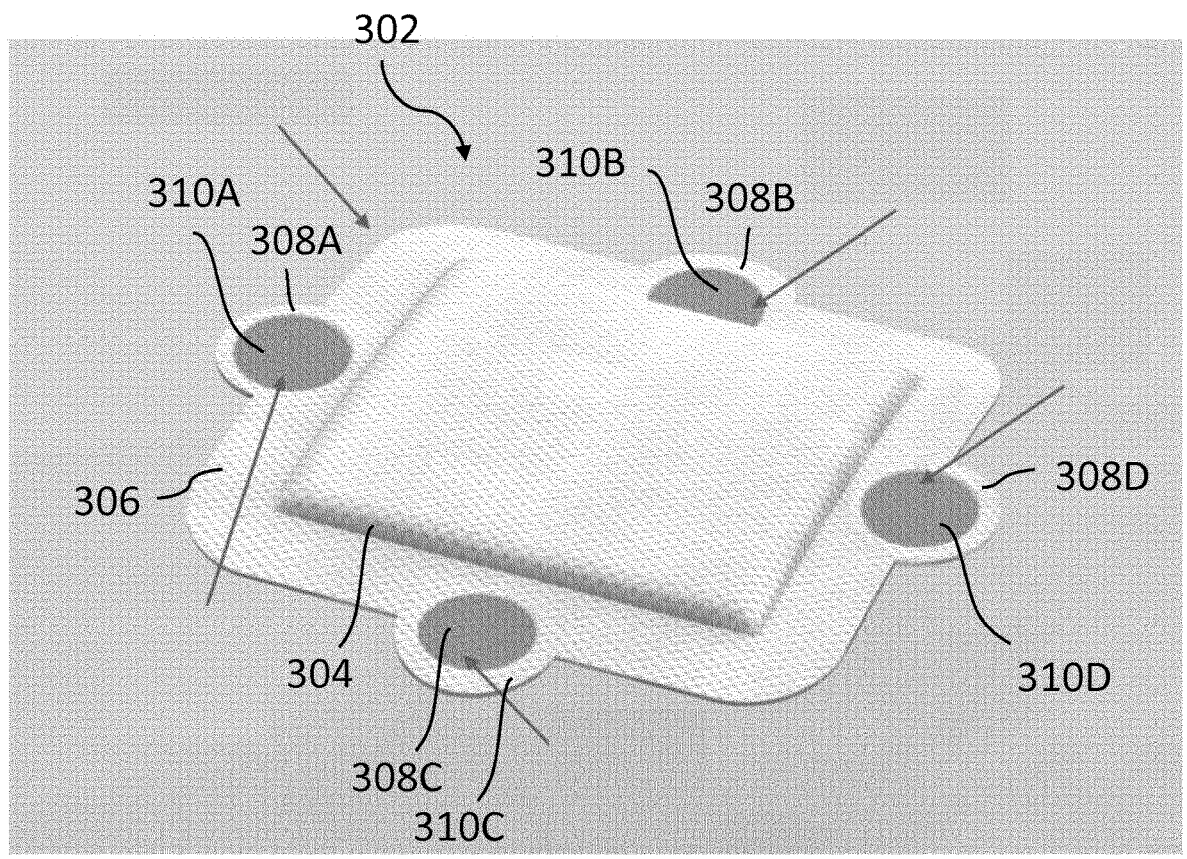
FIG. 9 shows a wound dressing.

FIG. 9 shows a wound dressing 302 comprising a wound protecting portion 304, a peripheral securing portion 306 and four sensor modules 308A, 308B, 308C, 308D. Each sensor module 308A, 308B, 308C, 308D is disposed at a respective lobe 310A, 310B, 310C, 310D of the peripheral portion 306. Each sensor module 308A, 308B, 308C, 308D comprises an optical sensor in accordance with the optical sensor shown in FIG. 3 for sensing an oxygen saturation ($SpO_2$) value at a target region of skin beneath the respective sensor. At least one of the sensor modules 308A, 308B, 308C, 308D comprises a motion sensor which can be used to determine whether measurements taken from all of the sensors should be stored or rejected. Alternatively, the motion sensor may be separate from the other sensor modules 308A, 308B, 308C, 308D.

In an alternative embodiment, an output from the optical sensor 20 may be analysed to determine whether a patient is active, or has been active, to an extent that an unreliable measurement would be expected. An analysis, such as a Fourier analysis, can be performed on a trace obtained over the predetermined period $T_S$ for at least one of the components of the output from the optical sensor. If signals at certain frequencies not associated with the frequencies of a typical pulse pressure waveform of the patient (for example at lower frequencies) are detected at significant amplitudes which are above expected levels of noise, it is determined that a motion artefact is present. The alternative embodiment therefore does not require a separate motion sensor.

Figure 10:
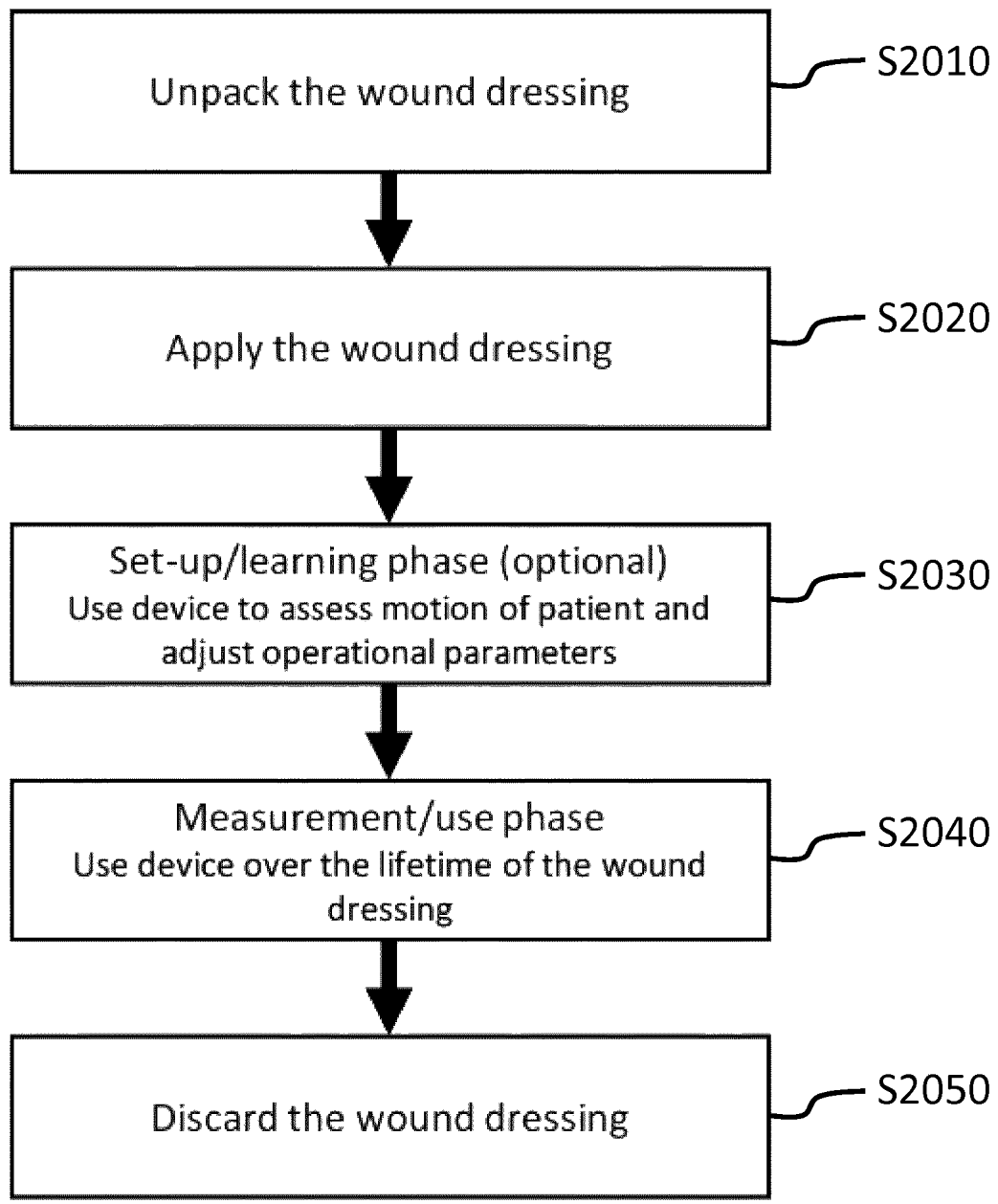
FIG. 10 is a flow chart showing steps associated with use of a wound dressing.

A learning process may be performed prior to operation of the apparatus 2 to establish suitable thresholds including a suitable predetermined period $T_S$ and a suitable threshold amplitude $A_{MAX}$ or whatever predetermined condition is used to determine the presence of a motion artefact. The thresholds can then be stored in the memory element 26 for subsequent recall by the first processor 24. The learning process may establish typical characteristics for a patient wearing the wound dressing, such as heart rate or amount of motion, for when the patient is motionless and/or resting. A flow chart depicting a method of using a wound dressing that incorporates a learning process is shown in FIG. 10. Firstly, at step S2010 the wound dressing of FIG. 1 is unpacked and then, at step S2020, the wound dressing is applied to a patient over a wound. At step S2030, an optional learning process is performed to set or adjust operational parameters such as the sample period and a threshold amplitude $A_{MAX}$. At step S2040 a method of determining an amount of skin perfusion in tissue surrounding a wound area, as described above, is then performed using the wound dressing. At step S2050, the wound dressing is removed, replaced if necessary by a fresh wound dressing, and discarded.

In another embodiment of the disclosure, in order to conserve energy, rather than acquiring data continuously, the sensor module is switched off for a period of time after successfully measuring a pulse rate or $SpO_2$ and is then woken up again at a future time by a user or a clinician or in accordance with an automated sequence to take another measurement.

In the embodiment descried above, a single axis accelerometer was used. However, in other embodiments, at least one multiple axis accelerometer could be used. It will be appreciated that at least one of the following techniques could be used to identify the presence of a motion artefact:

detection of whether the acceleration (either linear or angular) in one or more axes or a total acceleration, for example a combined acceleration in two or more axes, has exceeded a pre-determined, derived or adaptive threshold or else has deviated from a baseline by more than a multiple of a baseline noise amplitude;

detection of whether the velocity (either linear or angular) in one or more axes or a total velocity, for example a combined velocity in two or more axes, has exceeded a pre-determined, derived or adaptive threshold or else has deviated from a baseline by more than a multiple of a baseline noise amplitude;

detection of whether a displacement (either linear or angular) in one or more axes or a total displacement, for example a combined displacement in two or more axes, over the duration of the sample period or a part thereof has exceeded a pre-determined, derived or adaptive threshold or else has deviated from a baseline by more than a multiple of a baseline noise amplitude;

comparison of the standard deviation of the acceleration over the sample period or a part thereof against the typical noise level expected; this can be done for one or more axes of the coordinate system or for the total acceleration;

comparison of the standard deviation of the velocity over the sample period or a part thereof against the typical noise level expected; this can be done for one or more axes of the coordinate system or for the total acceleration and/or comparison of the amplitude at one or more frequencies or across a band around one or more frequencies against an expected level.

It will be appreciated that other types of motion sensors could be used such as single axis and/or multiple axes gyroscopes, inclinometers or the like. In other embodiments, a non-optical sensor may be used to sense a healing related parameter associated with wound healing.

The sensor modules described above may comprise one or more batteries as a power source or energy store. Additionally or alternatively, a range of other power sources may be used to provide power to the sensor module. Such alternatives may include, but are not exclusive to, capacitors, fuel cells or energy generators, which generate energy, for example, from the movement of the wearer, e.g. based on some piezo elements or the like, from temperature differences and heat generated by the user or the environment, using, for example, thermopiles, or from light, using, for example, photovoltaic cells, or other energy generating systems, for example clockwork type mechanisms which can be charged by the user. Any battery used may be non-rechargeable or rechargeable. Recharging can occur in a number of ways known to those trained in the art, including wired or contactless charging techniques.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

It will be understood that embodiments of the present disclosure are generally applicable for use in topical negative pressure ("TNP") therapy systems, such as be incorporated into a TNP dressing. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability. As is used herein, reduced or negative pressure levels, such as –X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of –X mmHg reflects absolute pressure that is X mmHg below 760 mmHg or, in other words, an absolute pressure of (760–X) mmHg. In addition, negative pressure that is "less" or "smaller" than X mmHg corresponds to pressure that is closer to atmospheric pressure (e.g., –40 mmHg is less than –60 mmHg). Negative pressure that is "more" or "greater" than –X mmHg corresponds to pressure that is further from atmospheric pressure (e.g., –80 mmHg is more than –60 mmHg). In some embodiments, local ambient atmospheric pressure is used as a reference point, and such local atmospheric pressure may not necessarily be, for example, 760 mmHg. The negative pressure range for some embodiments of the present disclosure can be approximately –80 mmHg, or between about –20 mmHg and –200 mmHg. Note that these pressures are relative to normal ambient atmospheric pressure, which can be 760 mmHg. Thus, –200 mmHg would be about 560 mmHg in practical terms. In some embodiments, the pressure range can be between about –40 mmHg and –150 mmHg. Alternatively a pressure range of up to –75 mmHg, up to –80 mmHg or over –80 mmHg can be used. Also in other embodiments a pressure range of below –75 mmHg can be used. Alternatively, a pressure range of over approximately –100 mmHg, or even –150 mmHg, can be supplied by the negative pressure apparatus.

In the drawings like reference numerals refer to like parts.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the disclosure are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The disclosure is not restricted to any details of any foregoing embodiments. The disclosure extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. An apparatus comprising:
   a wound dressing comprising a wound cover and a wound facing portion configured to be placed over a skin wound;
   a sensor patch releasably connected to a lateral side of the wound dressing, the sensor patch comprising at least one motion sensor configured to sense a motion related parameter associated with motion of the wound dressing;
   at least one further sensor configured to sense a healing related parameter associated with wound healing at a region of tissue of the wound or proximate the wound covered by the wound dressing; and
   a processor configured to:
      determine a sample period;
      determine that an output of the at least one motion sensor during the sample period satisfies a predetermined condition corresponding to a rate of acceleration of the wound dressing which is less than a predetermined rate of acceleration; and
      in response to determining that the output of the at least one motion sensor during the sample period satisfied the predetermined condition, determine the healing related parameter based on an output of the at least one further sensor during the sample period.

2. The apparatus of claim 1, wherein the healing related parameter is a parameter associated with blood perfusion within the region of tissue.

3. The apparatus of claim 1, wherein the healing related parameter is a parameter associated with oxygen saturation of blood within the region of tissue.

4. The apparatus of claim 1, wherein:
   the processor is configured to process an output of the at least one motion sensor, an output of the at least one further sensor, or both.

5. The apparatus of claim 4, wherein the wound dressing comprises a memory and the processor is configured to generate data which corresponds to an output of the at least one motion sensor and data which corresponds to an output of the at least one further sensor and to store said data in the memory.

6. The apparatus of claim 1, wherein the sensor patch is releasably connected to the lateral side of the wound dressing via a perforation line.

7. A wound monitoring method comprising:
   determining a sample period;
   sensing a motion related parameter associated with motion of a patient and a healing related parameter associated with wound healing at a region of tissue of the patient at or proximate to a skin wound, at least one of the motion related parameter or healing related parameter being sensed with a wound dressing comprising a wound cover, a wound facing portion configured to be placed over the wound, and a releasable sensor connected to a lateral side of the wound dressing;
   determining that the sensed motion related parameter satisfies a predetermined condition corresponding to a predetermined amount of motion of the patient; and
   storing, transmitting, or storing and transmitting data which represents the sensed healing related parameter associated with wound healing.

8. The method of claim 7, wherein the sensing the motion related parameter and healing related parameter comprises monitoring the motion related parameter and the healing related parameter over the sample period.

9. The method of claim 8, wherein the sample period is not less than one second or two seconds or five seconds or ten seconds.

10. The method of claim 8, wherein the sample period is not greater than sixty seconds or thirty seconds or fifteen seconds.

11. The method of claim 7, wherein the predetermined condition corresponding to the predetermined amount of motion of the patient is a condition in which the acceleration of the patient or the portion of the patient comprising the region of tissue at or proximate to the wound is below a threshold value.

12. The method of claim 7, wherein the motion related parameter is a pulse frequency of pulsatile arterial blood flow through the region of tissue and the predetermined condition corresponding to the predetermined amount of motion of the patient is a predetermined pulse frequency.

13. The method of claim 7, wherein the healing related parameter is associated with an amount of oxygen saturation at the region of tissue at or proximate to the wound.

14. The method of claim 7, wherein the stored data is data collected over the sample period in which the sensed motion related parameter satisfies the predetermined condition.

15. The method of claim 7, wherein the predetermined condition corresponding to the predetermined amount of motion of the patient is set based on attributes of the patient.

16. The method of claim 7, further comprising subsequently repeating sensing the motion and healing related parameters, determining that the motion related parameter satisfies the predetermined condition and storing data representing the parameter associated with wound healing to compile a plurality of records of data associated with wound healing.

17. The method of claim 16, further comprising transmitting the data comprising the plurality of records to a remote device for processing.

18. The method of claim 7, wherein the releasable sensor is releasably connected to the lateral side of the wound dressing via a perforation line.

19. An apparatus comprising:
   a wound dressing including a wound cover and a wound facing portion configured to be placed over a skin wound on a patient;
   at least one motion sensor configured to sense a motion related parameter;
   at least one further sensor configured to sense a healing related parameter associated with wound healing at a region of tissue of the wound or proximate the wound covered by the wound dressing; and a processor configured to process an output of the at least one motion sensor, an output of the at least one further sensor, or both, the processor further configured to:
set a sample period;
determine if the output of the at least one motion sensor satisfies a predetermined condition corresponding to a predetermined amount of acceleration of the patient or the portion of the patient comprising the region of tissue is below a threshold value;
in response to determining that the output of the at least one motion sensor satisfies the predetermined condition, retain data corresponding to the output of the at least one further sensor; and
in response to determining that that output of the at least one motion sensor fails to satisfy the predetermined condition, discard the data corresponding to the output of the at least one further sensor,
wherein the at least one motion sensor and the at least one further sensor are positioned on a separate portion releasably connected to a lateral side of the wound dressing.

20. The apparatus of claim 19, wherein the separate portion is releasably connected to the lateral side of the wound dressing via a perforation line.

* * * * *